United States Patent [19]
Azad et al.

[11] Patent Number: 6,054,126
[45] Date of Patent: *Apr. 25, 2000

[54] CLONING AND EXPRESSION OF HOST-PROTECTIVE IMMUNOGENS OF IBDV

[75] Inventors: Ahmed Abdullah Azad, Lower Templestowe; Peter John Hudson, Doncaster; Kevin John Fahey, Templestowe, all of Australia

[73] Assignee: Commonwealth Scientific and Industrial Research Organization, Campbell, Australia

[*] Notice: This patent is subject to a terminal disclaimer.

[21] Appl. No.: 07/902,846

[22] Filed: Jun. 23, 1992

Related U.S. Application Data

[63] Continuation of application No. 07/018,941, filed as application No. PCT/AU86/00156, May 30, 1986, abandoned.

[30] Foreign Application Priority Data

May 30, 1985 [AU] Australia .................... PH00815/85
Aug. 23, 1985 [AU] Australia .................... PH02118/85

[51] Int. Cl.[7] ............................ A61K 39/12; C07K 14/01
[52] U.S. Cl. .................................... 424/192.1; 424/204.1; 435/69.3; 435/69.7; 530/350; 530/395; 530/403
[58] Field of Search .............................. 530/300, 350, 530/395, 806, 826, 69.7, 403; 424/89, 192.1, 204.1; 435/69.1, 172.3, 69.3, 69.7; 514/2, 8

[56] References Cited

U.S. PATENT DOCUMENTS 4,237,224  12/1980  Cohen et al. ........................ 435/68
4,356,270  10/1982  Itakura ................................. 435/317

OTHER PUBLICATIONS

Hirai, K. V. et al. J. Virology 32:323–8 (1979), Further of Morphological Characterization and Structural Proteins of I.B.D.V.

Hudson, L. et al. *Practical Immunology* (1980). pp. 8–9. Blackwell Sci. Publications.

Jackwood, D.J. et al. Avian Dis. 28:990–1006 (1984) Nucleic Acid and Structural Proteins of I.B.D.V. Isolaters Belonging to Serotypes I and II.

MacReadie I.G. et al. Vaccine 8:549–552 (1990) "Passive Protection Against I.B.D.V. by Viral VP2 Expressed in Yeast.".

Becht, H. Curr. Top. Microbiol. Immunol. 90:107–121 (1980), "Infectious Bursal Virus Disease".

Dobos, P. J. Virology 32:1046–50 (1979), "Peptide Map Comparison of the Proteins of I.B.D.V.".

Fahey, K.J. et al. J. Gen. Virol. 66:1479–88 (1985) "Characterization by Western Blotting of the Immunogens of I.B.D.V.".

Fahey, K.J. et al. J. Gen. Virol. 66:2693–2702 (1985) "Antibody to the 32K Structural Protein of I.B.D.V. Neutralizes Viral Infectivity in Vitro and Confers Protection on Young Chickens.".

Müller, et al. J. Virology 44:384–92 (1982) Biosynthesis of Virus–Specific Protein in Cells Infected with I.B.D.V. and their Significance as Structural Elements for Infectious Virus and Incomplete Particles.

*Primary Examiner*—Thomas M. Cunningham
*Attorney, Agent, or Firm*—Bacon & Thomas

[57] ABSTRACT

This invention relates to the cloning and characterization of the infectious bursal disease virus (IBDV) genome, to the identification of cloned genes for host-protective antigens of IBDV, to the expression of cDNA inserts encoding the whole or part of host-protective antigens of IBDV in *E.coli* or other host cells, and to the use of the expressed antigens in the production of virus neutralizing antibodies in chickens. The invention also relates to the production of an effective sub-unit vaccine against IBDV utilizing the expressed antigens, as well as to the use of the expressed antigens in diagnostic tests, assays and the like.

14 Claims, 21 Drawing Sheets

←——————————————————————→
IBDV Large RNA Segment = 3400 b.p.

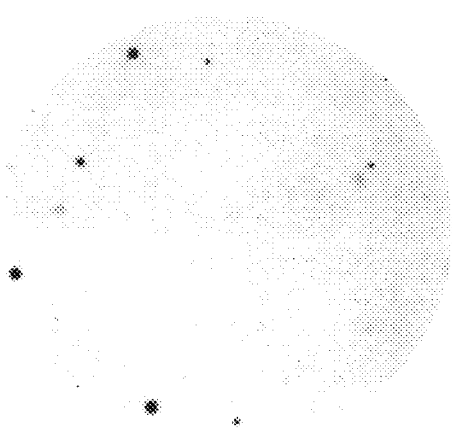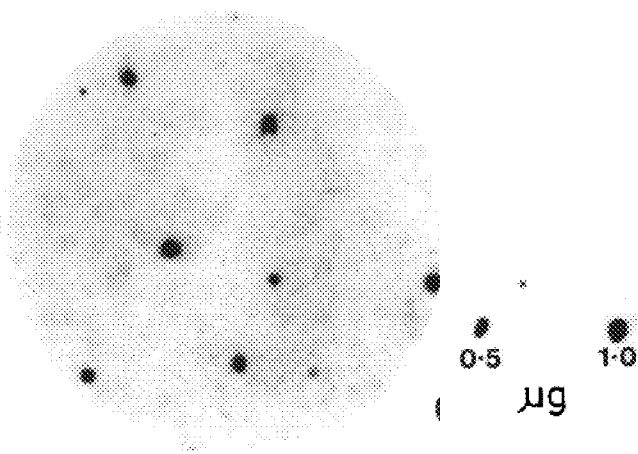
FIG. 3A   FIG. 3B   FIG. 3C (i) (ii) (iii) (iv) (v) (vi) (vii)(viii)　(i) (ii)(iii)(iv) (v) (vi)(vii)(viii)

FIG. 5

(i) (ii) (iii) (iv) (v) (vi) (vii)

(i) (ii) (iii) (iv) (v) (vi) (vii)

```
                                         ┌──────►G6
├──────►M7                              1
  -10                                   ┌─ ─ ─ ─ ─ ─
 V  E  I  R  Q  T  I  A  A  M   T  N  L  S  D  Q
AGTAGAGATCAGACAAACGATCGCAGCGATGACAAACCTGTCAGATCA

40
    ┌─ ─ ─►
 K   H  T  L  R  S  E  T  S  T  Y  N  L  T  V  G
AAGCACACTCTCAGGTCAGAGACCTCAACCTACAATTTGACTGTGGGG 80                        90
 N  Y  K  F  D  Q  M  L  L  T  A  Q  N  L  P
GGAACTACAAGTTCGACCAGATGCTCCTGACGGCTCAGAACCTACCAG

M7       L6              130
     ├──┤     ├──►
 G  T  I  N  A  V  T  F  Q  G  S  L  S  E  L  T
TGGCACCATAAACGCCGTGACCTTCCAAGGAAGCCTGAGTGAACTGAC

170          G6
                             ├──►
 T  V  L  S  L  P  T  S  Y  D  L  G  Y  V  R   L
ACCGTCCTCAGCTTACCCACATCATATGACCTTGGGTATGTGAGGCTT 210                       220
 T  A  A  D  D  Y  Q  F  S  S  Q  Y  Q  P  G
TAACTGCCGCAGATGATTACCAATTCTCATCACAGTATCAACCAGGTG

260
 V  Q  G  L  V  L  N  A  T  I  Y  L  V  G  F  D
CGTCCAAGGCCTTGTGCTAAACGCCACCATTTACCTGGTAGGCTTTGA

300
 V  I  P  T  S  E  I  T  Q  P  V  T  S  I  K  L
GTGATTCCAACCAGTGAGATAACCCAGCCAGTTACATCCATTAAACTG 340                           350
 G  G  N  Y  P  G  A  L  R  P  V  T  L  V  A
ATGGTGGAAACTACCCAGGTGCCCTCCGCCCCGTCACACTAGTAGCCT

390
 ┌─ ─ ─►                    ┌─ ─ ─►
  N  L  V  T  E  Y  G  R   F  D  P  G  A  M  N  Y
GAACCTAGTCACAGAATATGGCCGATTTGACCCAGGAGCCATGAACTA

─ ─►       430
 Y  F  M  E  V  A  D  L  N  S  P  L  K   I  A  G
TACTTCATGGAGGTGGCTGACCTCAACTCCCCCCTTAAGATTGCAGGA 470                       480
    L  A  H  A  I  G  E  G  V  D  Y  L  L  G  D
CCCTAGCCCATGCAATTGGGGAAGGTGTAGACTACCTGCTGGGCGATG
                                          520
```

*FIG. 10A*

```
       ___ ___ ___ 10 ___ ___ ___ ___ →                         20
       T   Q   I   V   P   F   I   R   S   L   L   M   P   T
    AACCCAGCAGATTGTTCCGTTTATACGGAGCCTTCTGATGCCAACA 50                              60
       D   T   G   S   G   L   I   V   F   F   P   G   F   P   G
    GACACAGGGTCAGGGCTAATTGTCTTTTTCCCTGGATTCCCCGGCT

100
       A   S   Y   N   Y   C   R   L   V   S   R   S   L   T   V   R
    CGAGCTACAACTATTGCAGGCTAGTGAGTCGGAGTCTAACAGTAAG 140                         150
       D   V   S   Y   N   G   L   M   S   A   T   A   N   I   N
    AGATGTTAGCTACAATGGCTTGATGTCCGCGACAGCCAACATCAAC

180 →                           190
       G   D   P   I   P   A   I   G   L   D   P   K   M   V   A
    GGTGACCCCATTCCTGCCATAGGACTCGACCCAAAAATGGTAGCCA

230
       G   V   T   I   T   L   F   S   A   N   I   D   A   I   T   N
    GAGTGACGATCACACTGTTCTCAGCCAACATTGATGCCATTACCAA 270                         280
       G   T   T   V   T   T   R   A   V   A   A   G   N   G   L
    TGGGACCACGGTAACCACCAGAGCTGTGGCCGCAGGCAATGGGCTG 310                         320
       E   I   V   T   S   K   S   G   G   Q   A   G   D   Q   M
    GAGATAGTAACCTCCAAAAGTGGAGGTCAGGCTGGAGATCAGATGT

360
       Y   E   R   V   A   T   G   S   V   V   T   V   A   G   V   S
    ATGAAAGAGTGGCAACAGGATCTGTTGTAACGGTCGCTGGGGTGAG 400                         410
       T   K   L   I   L   S   E   R   D   R   L   G   I   K  |T
    CACAAAACTAATCCTGAGTGAGAGGGACCGTCTTGGTATCAAGACC

440 →                           450
       A   F   G   F   K   D   I   I   R   A   I  |R   R| I   A
    GCTTTTGGCTTCAAAGACATAATCAGGGCCATAAGAAGGATAGCTG

490
       E  |A   Q   A   A   S   G| T  |A   R   A   A   S   G| K |A
    AGGCCCAGGCCGCTTCAGGAACTGCTCGAGCCGCGTCAGGAAAAGC
```

```
              30
 T  G  P  A  S  I  P  D  D  T  L  E
ACCGGACCGGCGTCCATCCCGGACGACACCCTGGAG

70
 S  I  V  G  A  H  Y  T  M  Q  S  N  G
CAATTGTAGGTGCTCACTACACGATGCAGAGCAATG 110                          120
  S  S  T  L  P  G  G  V  Y  A  L  N
GTCAAGCACACTCCCTGGTGGCGTTTATGCACTAAA

160
 D  K  I  G  N  V  L  V  G  E  G  V
GACAAAATTGGGAATGTCTTAGTAGGGGAAGGGGTC

200
 T  C  D  S  S  D  R  P  R  V  Y  T  I
CATGTGACAGTAGTGACAGGCCCAGAGTCTACACCA 240                          250
  L  S  V  G  G  E  L  V  F  Q  T  S
CCTCAGTGTTGGAGGAGAGCTCGTGTTCCAAACAAG

290
 T  A  G  T  D  N  L  M  P  F  N  L
ACGGCCGGCACCGACAACCTCATGCCATTCAACCTT

330
 S  W  L  A  S  G  N  L  A  V  T  I  H
CCTGGTTGGCAAGTGGGAACCTAGCAGTGACAATTC 370                          380
  N  F  E  L  I  P  N  P  E  L  A  K
CAACTTCGAGCTGATCCCGAATCCTGAGCTAGCCAA

420
 V  W  P  T  R  E  Y  T  D  F  R  E
GTCTGGCCAACAAGGGAGTACACCGACTTTCGTGAG

460
 V  P  V  V  S  T  L  F  P  P  A  A  P
TGCCGGTGGTTTCTACATTGTTCCCACCAGCCGCTC 500                          510
  R  A  A  S  G  R  I  R  Q  L  T  L
AAGAGCTGCCTCAGGCCGCATAAGGCAGCTAACTCT
              550
```

FIG. 10D

```
          A  A  D  K  G  Y  E  V  V  A  N  L  F  Q  V  P
         CGCAGCTGACAAGGGGTACGAGGTAGTTGCGAATCTATTCCAGGTGCC
                              560
       G  A  T  L  F  P  V  V  I  T  T  V  E  D  A  M
      GGTGCAACGTTATTCCCCGTTGTCATCACGACCGTGGAAGACGCCATG
              600                              610
       F  I  R  T  L  S  G  H  R  V  Y  G  Y  A  P
      CCTTCATACGAACTCTCTCCGGCCACAGGGTCTATGGCTATGCTCCAG
                              650
       K  D  P  I  P  P  I  V  G  N  S  G  N  L  A  I
      TAAAGACCCCATACCTCCCATTGTGGGGAACAGTGGCAATCTAGCCAT
                              690
       K  V  S  F  R  S  T  K  L  A  T  A  H  R  L  G
      AAAGTAAGCTTCAGAAGCACCAAACTCGCCACTGCACACCGACTTGGT
              730         L6              740
       R  D  W  D  R  L  P  Y  L  N  L  P  Y  L  P
      CACGCGACTGGGACAGGCTCCCCTACCTTAACCTCCCATATCTCCCTC
                              780
       M  E  A  A  A  D  V  D  P  L  F  Q  S  A  L  S
      CATGGAGGCGGCAGCCGACGTGGACCCACTGTTCCAATCCGCACTCAG
                              820
       R  N  F  L  A  N  A  P  Q  A  G  S  K  S  Q  R
      CGCAACTTTCTTGCAAACGCACCACAAGCAGGCAGCAAGTCGCAAAGA
              860                              870
       S  K  K  M  E  A  M  G  I  Y  F  A  T  P  E
      TCTCAAAGAAGATGGAGGCCATGGGCATCTACTTTGCAACACCAGAAT
                              910
       E  D  Y  L  D  Y  V  H  A  E  K  S  R  L  A  S
      CGAAGACTACCTAGACTATGTGCATGCAGAGAAGAGCCGGTTGGCATC
                              950
       V  A  K  V  Y  E  I  N  H  G  R  G  P  N  Q  E
      GTTGCCAAAGTCTATGAAATCAATCATGGGCGTGGCCCAAACCAAGAA
              990         D1              1000
       N  A  P  S  Q  R  P  P  G  R  L  G  R  W  I
      CCAATGCTCCATCACAGAGACCCCCTGGTCGGCTGGGCCGCTGGATCA
          D6
      CTAGTAACA
```

```
         Q  N  P  V  V  D  G  I  L  A  S  P  G  V  L
        CCAGAATCCCGTAGTTGACGGAATTCTTGCCTCACCTGGAGTGCTC 570                              580
         T  P  K  A  L  N  S  K  M  F  A  V  I  E  G
        ACACCCAAAGCACTGAACAGCAAGATGTTTGCTGTCATTGAAGGCG

620
         D  G  V  L  P  L  E  T  G  R  D  Y  T  V  V  P
        ATGGGGTGCTCCCTCTGGAGACCGGGAGAGACTACACTGTTGTCCC 660                       670
         A  Y  M  D  V  F  R  P  K  V  P  I  H  V  A
        AGCCTACATGGATGTATTCAGACCCAAGGTTCCCATCCATGTAGCT

700       D6                     710
         L  K  L  A  G  P  G  A  F  D  I  N  T  G  P
        CTCAAGTTGGCTGGGCCTGGTGCATTTGACATAAACACCGGGCCCA

750
         P  S  A  G  R  Q  Y  H  L  A  M  A  A  S  E  F
        CCAGTGCAGGACGCCAATACCATCTTGCCATGGCCGCCTCAGAGTT 790                       800
         V  F  M  W  L  E  E  N  G  I  V  T  D  M  A
        TGTGTTCATGTGGCTAGAAGAAAACGGGATTGTGACCGACATGGCC 830                              840
         A  K  Y  G  T  A  G  Y  G  V  E  A  R  G  P
        GCCAAGTACGGAACAGCAGGTTACGGCGTGGAGGCCAGGGGCCCCA

880
         W  V  A  L  N  G  H  R  G  P  S  P  G  Q  L  K
        GGGTAGCACTCAATGGGCACCGAGGGCCAAGCCCTGGCCAGCTAAA 920                       930
         E  E  Q  I  L  R  A  A  T  S  I  Y  G  A  P
        AGAAGAACAGATCCTACGGGCCGCCACCTCGATCTACGGGGCTCCA 960                              970
         Q  M  K  D  L  L  L  T  A  M  E  M  K  H  R
        CAGATGAAAGATCTGCTCTTGACTGCGATGGAGATGAAGCATCGCA

1010
         R  T  V  S  D  E  D  L  E  *
        GAACGGTCTCTGACGAGGACCTTGAGTAAGGCTCCTGGGAGTCTCC
```

FIG. IOE

```
          R  G  A  H  N  L  D  C  V  L  R  E
          CGCGGTGCACACAACCTCGACTGCGTGCTAAGGGAG

590
       V  R  E  D  L  Q  P  P  S  Q  R  G  S
       TGCGAGAAGACCTCCAACCTCCATCTCAAAGAGGAT 630                           640
       I  D  D  V  W  D  D  S  I  M  L  S
       AATAGACGATGTATGGGACGACAGCATCATGCTGTC

680
          M  T  G  A  L  N  A  Y  G  E  V  E
          ATGACAGGAGCCCTCAATGCCTACGGCGAAGTTGAG

720
       N  W  A  T  F  I [K  R] F  P  H  N  P
       ACTGGGCGACGTTCATCAAACGTTTCCCCCACAATC 760                            770
          K  E  T  P  E  L  E  S  A  V  R  A
          CAAAGAGACCCCCGAACTCGAAAGTGCCGTCAGAGC

810
          N  F  A  L  S  D  P  N  A  H  R  M
          AACTTTGCACTCAGCGACCCAAACGCCCATCGGATG

D1         850
       T  P  E  E  A  Q  R  E  K  D  T  R  I
       CACCAGAGGAGGCCCAGAGGGAAAAAGACACTCGGA 890                             900
          Y  W  Q  N  T  R  E  I  P  D  P  N *
          GTACTGGCAGAACACACGAGAAATACCAGACCCAAA

940
       G  Q  A  E  P  P  Q  A  F  I  D  E
       GGACAGGCAGAGCCACCCCAAGCATTCATAGATGAA

980
       N  P [R  R] A  P  P  K  P  K  P  K  P
       ATCCCAGGCGGGCTCCACCAAAGCCCAAGCCAAAAC

CGACACCACCCGCGCAGGTGTGGACACCAATTCGGC
```

FIG. 10F

FIG. 15  CORRECT PROCESSING OF 32 Kd ANTIGEN

FIG. 16

CLONING AND EXPRESSION OF HOST-PROTECTIVE IMMUNOGENS OF IBDV

This application is a Continuation of application Ser. No. 07/018,941, filed Jan. 29, 1987 now abandoned, which is a 35 USC 371 national application of PCT/AU86/00156, filed May 30, 1986.

This invention relates to the cloning and characterisation of the infectious bursal disease virus (IBDV) genome, to the identification of cloned genes for host-protective antigens of IBDV, to the expression of cDNA inserts encoding the whole or part of host-protective antigens of IBDV in *E.coli* or other host cells, and to the use of the expressed antigens in the production of virus neutralizing antibodies in chickens. The invention further relates to the production of an effective sub-unit vaccine against IBDV utilising the expressed antigens, as well as to the use of the expressed antigens in diagnostic tests, assays and the like.

In one particularly preferred aspect, this invention relates to a method for the use of recombinant DNA techniques in the production of "correctly" processed antigens of IBDV. The production of such "correctly" processed antigens is of particular importance in ensuring, for example, that these antigens may be effectively used as vaccine components for the production of neutralising and protective antibodies.

The polypeptides of an Australian strain (002-73) of IBDV have recently been characterised. In prior International Patent Specification No. PCT/AU84/00256, it is disclosed that the 32 Kd structural protein is a major immunogen of IBDV, and produces antibodies in chickens that neutralize the virus in vitro and protect the chickens from IBDV infection.

Further work has now led to the characterisation and molecular cloning of the genome of IBDV strain 002-73, and this genome has been shown to consist of two segments of double-stranded (ds) RNA which are approximately 3400 b.p. (MW $2.06 \times 10^6$) and 2900 b.p. (MW $1.76 \times 10^6$) long, respectively. In vitro translation studies show that the large RNA segment codes for three major structural proteins, including the 32 Kd host-protective antigen previously identified. A novel method for the cloning of long double-stranded RNA molecules has been developed and used to clone the entire genome of IBDV. Molecular hybridization and expression studies involving cloned cDNA inserts have allowed the identification of the region of the IBDV genome that codes for the 32 Kd host-protective antigen. Cloned genes encoding the entire or part of this antigen have been sequenced and expressed in *E.coli*. In addition the immunogenicity in chickens of the expressed polypeptides has been tested, as well as their ability to produce virus neutralising antibodies.

Initial work in this regard has lead to the production of the 32 Kd host-protective antigen of IBDV in the form of fusion proteins. The test results show that the fusion proteins are highly immunogenic and produce antibodies that recognise denatured 32 Kd protein. These antibodies, however, have weak ELISA and virus neutralising titres. The fusion proteins react strongly with MAb 17-80 (monoclonal antibody that recognises denatured 32 Kd viral protein), but weakly with the virus neutralising MAb 17-82. These results suggest that these genetically engineered fusion proteins may not have the correct three-dimensional structure necessary for the production of virus neutralising and protective antibodies, or that other viral proteins possess epitopes or are important in the formation of epitopes involved in the neutralisation of whole virus.

Further work has shown that a monoclonal antibody (MAb 17-82), that neutralises the infecivity of IBDV, recognises an epitope encoded within the gene for the 52 Kd precursor protein; a protein processed into the 41 Kd and 37 Kd structural proteins of IBDV. The expressed polypeptide from the 52 Kd region that reacts with MAb 17-82, does not contain epitopes recognised by the monoclonal antibody specific for the 32 Kd structural protein (MAb 17-80).

According to one aspect of the present invention, there is provided a recombinant DNA molecule comprising a nucleotide sequence substantially corresponding to all or a portion of IBDV RNA, particularly the IBDV RNA segment of approximately 3400 b.p. Preferably, the nucleotide sequence codes for all or part of at least one structural protein of IBDV. In one particular aspect of the invention, the DNA molecule is capable of being expressed as a polypeptide displaying antigenicity substantially corresponding to the 32 Kd or 41/37 Kd structural protein of IBDV.

By way of exemplification of this aspect of the invention, the nucleotide sequence may be characterised by at least a portion thereof having the base sequence substantially as shown in FIG. 10 hereinafter or one or more portions of said base sequence.

The complete nucleotide sequence of the large segment of the IBDV genome and the amino acid sequence derived from it are shown in FIG. 10.

Translation, in vitro, of the IBDV large segment genomic RNA in rabbit reticulocyte and wheat germ cell-free systems has led to the synthesis of discrete polypeptides identical in size to the viral proteins although there is only one stop codon at the 3' end of the large segment of the IBDV genome. While the rabbit reticulocyte and wheat germ cell-free systems may contain protease(s) which help to process viral polyproteins, it would appear more likely that one of the polypeptides encoded by the IBDV genome is a specific protease. Further work in this regard has enabled the production of correctly processed 32 Kd or 41/37 Kd protein of IBDV instead of the fused proteins described above.

Accordingly, in a particularly preferred embodiment of this invention, there is provided a recombinant DNA molecule comprising a nucleotide sequence coding for all or part of the 32 Kd structural protein or the 52 Kd precursor protein of IBDV, together with further portion(s) of the 3400 b.p. segment coding for further polypeptides or proteins to correctly process said 32 Kd or 41/37 Kd structural protein. Expression of this molecule leads to the expression of the 32 Kd or 41/37 Kd structural protein as a correctly processed protein. Such a molecule may encode both the 32 Kd structural protein as well as additional polypeptides or proteins, including proteases, required to correctly process the 32 Kd structural protein.

It will be appreciated that the nucleotide sequence of this aspect of the invention may be obtained from natural, synthetic or semi-synthetic sources, or by manipulation of the natural material; furthermore, this nucleotide sequence may be a naturally-occurring sequence, or it may be related by mutation, including single or multiple base substitutions, deletions, insertions and inversions, to such a naturally-occurring sequence, provided always that the DNA molecule comprising such a sequence is capable of being expressed as a polypeptide displaying the antigenicity of one or more structural proteins of IBDV.

The nucleotide sequence may have expression control sequences positioned adjacent to it, such control sequences being derived either from IBDV nucleic acid or from a heterologous source.

This invention also provides a recombinant DNA molecule comprising an expression control sequence having promoter sequences and initiator sequences, and a nucleotide sequence coding for all or part of at least one structural protein of IBDV.

In yet another aspect, the invention provides a recombinant DNA cloning vehicle capable of expressing all or part of at least one structural protein of IBDV, comprising an expression control sequence having promotor sequences and initiator sequences, and a nucleotide sequence coding for all or part of at least one structural protein of IBDV.

In a further aspect, there is provided a host cell containing a recombinant DNA cloning vehicle and/or a recombinant DNA molecule as described above.

In yet further aspects, there are provided polypeptides displaying IBDV antigenicity which can be produced by a host cell transformed or infected with a recombinant DNA cloning vehicle as described above. Such expressed polypeptides may comprise all or part of at least one structural protein of IBDV as derived from the base sequence substantially as shown in FIG. 10 or one or more portion(s) of the said sequence. Such polypeptides can be isolated from the host cell, and if necessary purified to provide the polypeptide substantially free of host cell or other proteins. Where the expressed polypeptides are in the form of a fused polypeptide, they may be cleaved to remove the "foreign" peptide portion.

It will be appreciated that such expressed polypeptides as described above may be constructed by permutation and combinations of portions of the nucleotide sequence presented in FIG. 10.

The present invention also extends to synthetic peptides or polypeptides displaying the antigenicity of all or a portion of at least one structural protein of IBDV, particularly the 32 Kd and/or 41/37 Kd structural proteins.

As used herein, the term "synthetic" means that the peptides or polypeptides have been produced by chemical and/or molecular biological means, such as by means of chemical synthesis or by recombinant DNA techniques leading to biological synthesis. Such polypeptides can, of course, be obtained by direct expression by a host-cell of a correctly processed and folded protein, or by cleavage of a fused polypeptid (an IBDV polypeptide fused to a non-IBDV polypeptide) produced by a host cell and separation of the desired Polypeptide from additional polypeptide coded for by the DNA of the host cell or cloning vehicle by methods well known in the art. Alternatively, once the amino acid sequence of the desired polypeptide has been established, for example, by determination of the nucleotide sequence coding for the desired polypeptide, the polypeptide may be produced synthetically, for example by the well-known Merrifield solid-phase synthesis procedure [Marglin and Merrifield, (1970)].

It will be appreciated that polypeptides displaying antigenicity characteristic of structural proteins of IBDV will have utility in serological diagnosis, and in the preparation of single or multivalent vaccines against IBDV by methods well known in the art of vaccine manufacture. Further details of such vaccines, and of methods of use thereof, as well as of quantitative and qualitative assays, are disclosed in International Patent Specification No. PCT/AU84/00256.

BRIEF DESCRIPTION OF THE DRAWINGS

The following detailed description relates to the characterization and molecular cloning of the genome of IBDV strain 002-73. In the accompanying diagrams:

FIGS. 2A and 2B are a map of cloned inserts covering the entire large RNA segment of IBDV.

FIGS. 3A–3C show some E.coli colonies expressing proteins positive to a monoclonal antibody (Mab 17–80) that reacts with denatured 32Kd protein of IBDV.

FIGS. 4A and 2B show proteins from E.coli colonies subjected to electrophoresis and (a) stained with Coomassie Blue, or (b) Western blotted and reacted with Mab 17–80. Arrows 1 and 2 indicate the positions of fusion protein and β-galactosidase, respectively. Samples are (i) HB 101 cells, (ii) HB 101 with pUR 290, (iii)–(viii) some recombinant clones that were identified as possible positives by reaction with MAb 17–80(FIG. 3).

FIG. 5 shows the position of the insert from clone D6 on the large segment of IBDV genome; the restriction map of the inserts from clones D6 and D1.

FIG. 10A–10F show sequence analysis of the large RNA segment of IBDV. The predicted amino acid sequence is presented in single letter code above the nucleotide sequence derived from cDNA clones. There are no other extensive open reading frames. The amino acid sequences are numbered sequentially from the N-terminus of the 37Kd protein as position 1. The region encompassed by cDNA clones M7, G6, L6, D6 and D1 are indicated. Dibasic residues are boxed and the repeat unit A-X-A-A-S is similarly highlighted. N-terminal sequences derived from tryptic peptides are shown overlined as (- - - - >) for the 37Kd, (. . . . >) for 28Kd and (- - - - >) for the 32Kd protein. Only the N-terminus of the 37Kd protein could be obtained by direct sequencing on intact proteins and this is shown from residue 1.

FIG. 15 indicates the minimum size of precursor polypeptide that has to be expressed for the correct processing of the 32Kd antigen. The insert of clone PO, that contains the entire coding region of the large segment of IBDV genome, was progressively shortened at the 5' end at specific restriction sites and the resultant fragments were expressed in pPL vector in *E.coli*. Expressed gene products were Western blotted and reacted with Mab 17–80.

FIG. 16 indicates the regions of the precursor polypeptide that may contribute to the antigenic determinant recognised by the virus neutralising monoclonal Mab 17–82. Undenatured proteins from clones containing precursors of varying sizes were blotted onto nitrocellulose filter and reacted with Mab 17–80 or Mab 17–82.

MATERIALS AND METHODS

Figure 1:
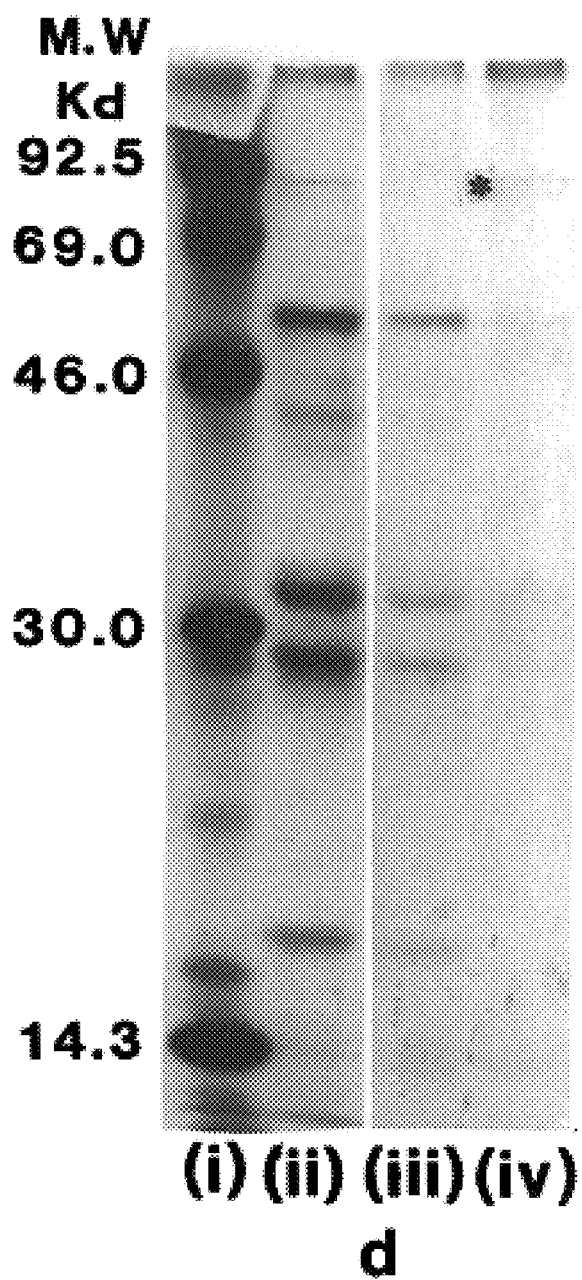
FIG. 1 shows electrophoresis of IBDV RNA translation products synthesised in rabbit reticulocyte lysate, particularly the MW of translation products and coding assignments of IBDV RNA segments (i) MW standards; (ii) unfractionated IBDV RNA; (iii) large segment of IBDV RNA; (iv) small segment of IBDV RNA.

Materials and their sources are Klenow fragment of DNA polymerase 1, S1 nuclease, DNase 1, and RNase A (Boehringer); rabbit reticulocyte lysate, [$\alpha$-$^{32}$P]ATP, [$\gamma$-$^{32}$P]ATP, [$^{35}$S]methionine, and PstI (Amerisham); RNase-free sucrose, DNA polymerase 1, and wheat germ lysate (Bethesda Research Laboratories); RNase-free Pronase (Calbiochem); agarose and lysozyme (Sigma); low melting point agarose and SDS (Bio-Rad), diethylpyrocarbonate and acridine orange (Merck); nitrocellulose filters and NA45 membrane filters (Schleicher and Schuell); reverse transcriptase (RTase) (Life Sciences Inc., St. Petersburg, Fla.); terminal transferase (Ratliffe, Los Alamos, N. Mex.); RNasin (Promega Biotech, Madison, Wis.). Random primers were prepared from sheep DNA by the method described by Taylor et al. (1976). UK bovine rotavirus ds RNA was prepared by Dr. M. Dyall-Smith. Virus: IBDV strain 002-73 was first reported by Firth (1974) in commercial chicken flocks in Australia and confirmed as IBDV at the Central Veterinary Laboratory, Weybridge, U.K. The virus was routinely passaged in 4- to 6-week old SPF White Leghorn chickens, isolated from bursas 3 days after infection, and purified by successive fractionations on sucrose and CsCl gradients.

Isolation and Purification of IBDV RNA

Homogenates of fresh infected bursas were spun at 17,000 g for 15 minutes at 0°. The clear supernatant was layered on top of 2-ml sucrose cushions (40%) and the virus particles were pelleted through the cushions in a Beckman SW40 rotor at 22,000 rpm at 2° for 2.5 hours. The pellets were suspended in 10 mM Tris. pH 7.5, 10 mM NaCl, 10 mM EDTA, 0.2% SDS, and 0.1% diethylpyrocarbonate and diaested with RNase-free Pronase (1 mg/ml) for 1 hour at 37°, The solution was extracted with phenol and chloroform (1:1) and the RNA in the aqueous phase recovered by precipitation with ethanol. The ds viral RNA was purified from the chicken cellular RNA by differential salt precipitation (Diaz-Ruiz and Kaper, 1978).

Individual RNA or DNA segments were isolated from agarose gels by electrophoresis onto NA45 membrane filters followed by elution in 1M NaCl and 0.05 M arginine at 70°. Alternatively, RNA bands were excised from low melting point agarose slab gel and melted (70°) in 5 mol. of low salt buffer containing 0.5% SDS. The solution was extracted with phenol and the RNA in the aqueous phase precipitated with ethanol.

Hybridization Probes

IBDV RNA was labeled with [$\gamma$-$^{32}$P] following mild alkaline digestion (Goldbach et al. 1978). cDNA probes were prepared from denatured ds RNA using random primers to initiate cDNA synthesis in the presence of RTase. The RNA template was then destroyed by digestion with NaOH. Nick translation of cloned DNA fragments was carried out essentially as described by Rigby et al. (1977). All radioactively labeled probes were purified from unreacted isotopes by precipitation (3x) from 2 M ammonium acetate and isopropanol at room temperature.

Translation of IBDV RNA in vitro

IBDV RNA (1–2 $\mu$g) in 3 $\mu$l of 10 mM phosphate, pH 6.8 was heated at 100° for 2 minutes and snap chilled in dry ice/ethanol. Methylmercuric hydroxide (1 $\mu$l of 40 mM) was then added and the mixture left at room temperature for 10 minutes. $\beta$-Mercaptoethanol (1 $\mu$l of 700 mM) and 1 $\mu$l of RNasin (25 units) were added and the solution was incubated for a further 5 minutes at room temperature. Aliquots (1 $\mu$l) were transferred to tubes containing 5 $\mu$Ci of [$^{35}$S] methionine (dried down) and 30 $\mu$l of rabbit reticulocyte lysate and the solution was incubated at 30° for 1 hour. The reaction mixture was reacted in succession with chicken antiserum, rabbit anti-chicken IgG, and protein A-Sepharose (Pharmacia). The protein A-Sepharose-antigen-antibody complex was washed extensively with phosphate-buffered saline containing 0.1% NP-40 and then boiled in buffer containing 2% SDS. The protein A-Sepharose was spun down and the translated proteins in the supernate were analysed by polyacrylamide gel electrophoresis (12.5% gel). The gel was then treated with AMPLIFY (Amersham), dried and exposed to Fuji RX film with intensifying screen (Dupont Cronex Lightening Plus AA).

Synthesis of ds cDNA from ds RNA.

IBDV RNA (5 $\mu$g) in 9 $\mu$; pf 5 mM phosphate buffer, pH 6.8, was heated at 1000 for 2 minutes and then snap frozen. After the RNA had thawed 1 $\mu$l of 100 mM methylmercuric hydroxide was added and the mixture left at room temperature for 10 minutes. Two microliters of RNasin (50 units) and 4 $\mu$l of 700 mM $\beta$-mercaptoethanol were then added and the mixture was left at room temperature for a further 5 minutes. Ten microliters of random primers (50 $\mu$g), which had been separately denatured by boiling and snap chilling, was then added to the mixture to prime cDNA synthesis. The mixture (100 $\mu$l final volume) contained RTase (50 units) and other reactants required for cDNA synthesis. Following incubation at 42° for 2 hours the RNA template was destroyed by digestion with NaOH, and the cDNA purified by gel filtration. Complementary cDNA fragments were annealed in 0.3 M NaCl at 65° for 2 hours following initial heating at 90° for 3 minutes. The solution was then allowed to cool gradually to room temperature over 1 hour. The annealed cDNA segments were repaired and chains. extended with DNA polymerase 1. The ds cDNA chains were further extended with RTase, treated with DNA ligase and S1 nuclease, and finally purified by gel filtration.

Cloning of IBDV ds cDNA

The ds cDNA was C tailed with terminal transferase, annealed to G-tailed Pst-cut pBR322 (New England Nuclear), and cloned in *Escherichia coli* RR1 cells. The recombinant colonies were hybridized with radioactive probes made from IBDV RNA segments and autoradiographed. Biological containment levels specified by the Australian Recombinant DNA Monitoring Committee were used.

Isolation of Plasmid DNA

Plasmid DNA was isolated essentially by the Ish-Horowicz and Burke (1981) modification of the method described by Birnboim and Doly (1979) with the following further modifications. RNase digestion was carried out concommitantly with lysozyme treatment, and the plasmid DNA was purified from RNA breakdown products by precipitation from polyethylene glycol (6.5% PEG, 0.8 M NaCl, 0°, 1 hour).

Colony Hybridization

The recombinant colonies were hybridized with radioactive probes as described by Grunstein and Hogness (1975). The solution used for prehybridization and hybridization contained 5×Denhardt's solution, 10 mM HEPES (pH 7.0), 0.1% SDS, 3×SSC, 10 μg/ml E. coli tRNA, and 18 μg /ml sonicated and denatured herring sperm DNA. The filters were prehybridized at 65° for 2 hours, and then hybridized with radioactive probes for 16–20 hours at 65°. The filters were washed 4×30 minutes with 0.5×SSC,0.1% SDS at 65°, and then autoradiographed using Fuji RX film and intensifying screen.

Results

1. Isolation and purification of RNA. The RNA isolation procedure described above is simple and rapid, and results in a high yield of good quality RNA. A low-speed spin of the bursal homogenate followed by sedimentation of the virus particles through a 40% sucrose cushion resulted in the removal of virtually all the cellular DNA and over 90% of the cellular RNA. Following digestion with Pronase and extraction with phenol and chloroform, the total RNA was fractionated by differential salt precipitation (Diaz-Ruiz and Kaper, 1978). The cellular ss RNA was precipitated from 2 M LiCl and the viral ds RNA in the supernatant could be further purified from low MW contaminants and any contaminating DNA by precipitation from 4M LiCl.

2. Physico-chemical characterization of the viral genome. To determine whether the RNA of the Australian isolate IBDV 002-73 is double stranded, viral RNA which had not been totally purified from single-stranded cellular RNA was electrophoresed under nondenaturing conditions, stained with acridine orange, and the nucleic acid bands were visualized on a uv transilluminator. The DNA standards, ds UK bovine rotavirus RNA segments, and the two segments of IBDV RNA in the upper part of the gel appeared as bright green bands as expected of ds nucleic acids (Lerman, 1963), while the single-stranded cellular RNA near the bottom of the gel appeared bright red (Blake and Peacocke, 1968). Moreover, under RNase A-digestion conditions that completely destroy 28 S and 18 S rRNA the two segments of IBDV RNA remained intact when electrophoresed under nondenaturing conditions. Thus, the genome of IBDV strain 002-73 consists of two segments of ds RNA as has been shown to be the case for strain Cu-1 (Muller et al, 1979) and a strain isolated at the Central Veterinary Laboratories, Weybridge, U.K. (Todd and McNulty, 1979).

When electrophoresed under nondenaturing conditions the two segments of IBDV RNA appear to be 3825 and 3400 bp, respectively, when compared with DNA standards. These values correspond to MW of $2.52 \times 10^6$ and $2.2 \times 10^6$, respectively, for the two segments. When compared under nondenaturing conditions with ds RNA segments of UK bovine rotavirus, the sizes of which were obtained by electron microscopy (Rixon et al, 1984), the two segments of IBDV ds RNA appear to be about 3400 bp (MW $2.06 \times 10^6$) and 2900 bp (MW $1.76 \times 10^6$), respectively.

3. Translation, in vitro, of IBDV RNA. The ds RNA has to be extensively denatured for any in vitro protein synthesis to take place. Heating at 100° followed by snap chilling in dry ice/ethanol was not sufficient, and heating the RNA in 90% dimethylsulfoxide gave inconsistent results. The best results were obtained when the heat-denatured RNA was further denatured in 10 mM methylmercuric hydroxide. Even after these treatments the amount of radioactivity incorporated into TCA-precipitable material was only between 10 and 20% of that obtained when translating similar amounts of rotovirus ss RNA or globin mRNA.

Immunoprecipitation of the translation product shows that total IBDV RNA codes for six polypeptides of Ca. MW 90 Kd, 52 Kd, 41 Kd, 32 Kd, 18 Kd, and 16 Kd (FIG. 1 (ii). The larger RNA segment, purified by gel electrophoresis, produces all the translation products except the 90-Kd polypeptide (FIG. 1 (iii). When the smaller RNA segment, which we have not been able to completely purify by gel electrophoresis, is translated in vitro traces of all the translation products are seen but the 90-Kd protein is consistently the most prominent one (FIG. 1 (iv). Since this 90-Kd protein is consistently absent among the translation products of the larger RNA segment it would appear that all the IBDV proteins except the 90-Kd protein are encoded by the larger RNA segment.

4. Molecular cloning of IBDV ds DNA. To overcome problems encountered in the synthesis of cDNA covering the entire IBDV genome an alternative method was developed for the cloning of long ds RNA molecules. The ds RNA was denatured in methylmercuric hydroxide and random primers were used to initiate cDNA synthesis on both strands of the RNA simultaneously in the presence of RTase. The RNA was then destroyed and complementary cDNA strands were allowed to reanneal. DNA polymerase 1 was used to repair and extend the cDNA chains, which were then extended further with RTase. The ds cDNA molecules were then treated with DNA ligase followed by S1 nuclease. The ds cDNA molecules were C tailed and annealed to G-tailed pBR322, and used to transform E.coli RR1 cells.

Recombinant colonies were hybridized with radioactive probes made from the large or small segment of IBDV RNA, and 200 colonies positive to each of the probes were randomly selected for further characterization. The positive colonies were screened a for plasmid size by electrophoresing colony lysates on agarose mini-gels. A few of these colonies, positive to the large segment probes, were grown up in 5 ml L broth for plasmid DNA isolation. The plasmids were digested with PstI and the sizes of the inserts determined by electrophoresis. These inserts of defined size were "nick translated" and used separately to probe identical sets of positive colonies. Inserts from clones D6 (1100 bp), L6 (1900 bp), and M7 (450 bp) hybridized with three basically different sets of colonies. Inserts from clone G2 (1600 bp) hybridized to colonies which previously hybridized either with D6 or L6 probe but not with both. Similarly, a N9 insert (950 bp) hybridized with colonies which were positive either to the L6 or M7 probes but not to both. From the sizes of the insert and the extent and ability to cross-hybridize with colonies positive to the large RNA segment it was possible to construct a tentative map to show that overlapping cDNA fragments covering the entire large RNA segment had been cloned (FIG. 2), and the relative positions of all the positive colonies could be determined on this map.

The following detailed description relates to the expression in E.coli of cDNA fragments encoding the gene for the host-protective antigen of IBDV. In the accompanying diagrams:

FIGS. 3A–3C show some E.coli colonies expressing proteins positive to a monoclonal antibody (Mab 17-80) that reacts with denatured 32 Kd protein of IBDV.

Figures 4A, 4B:
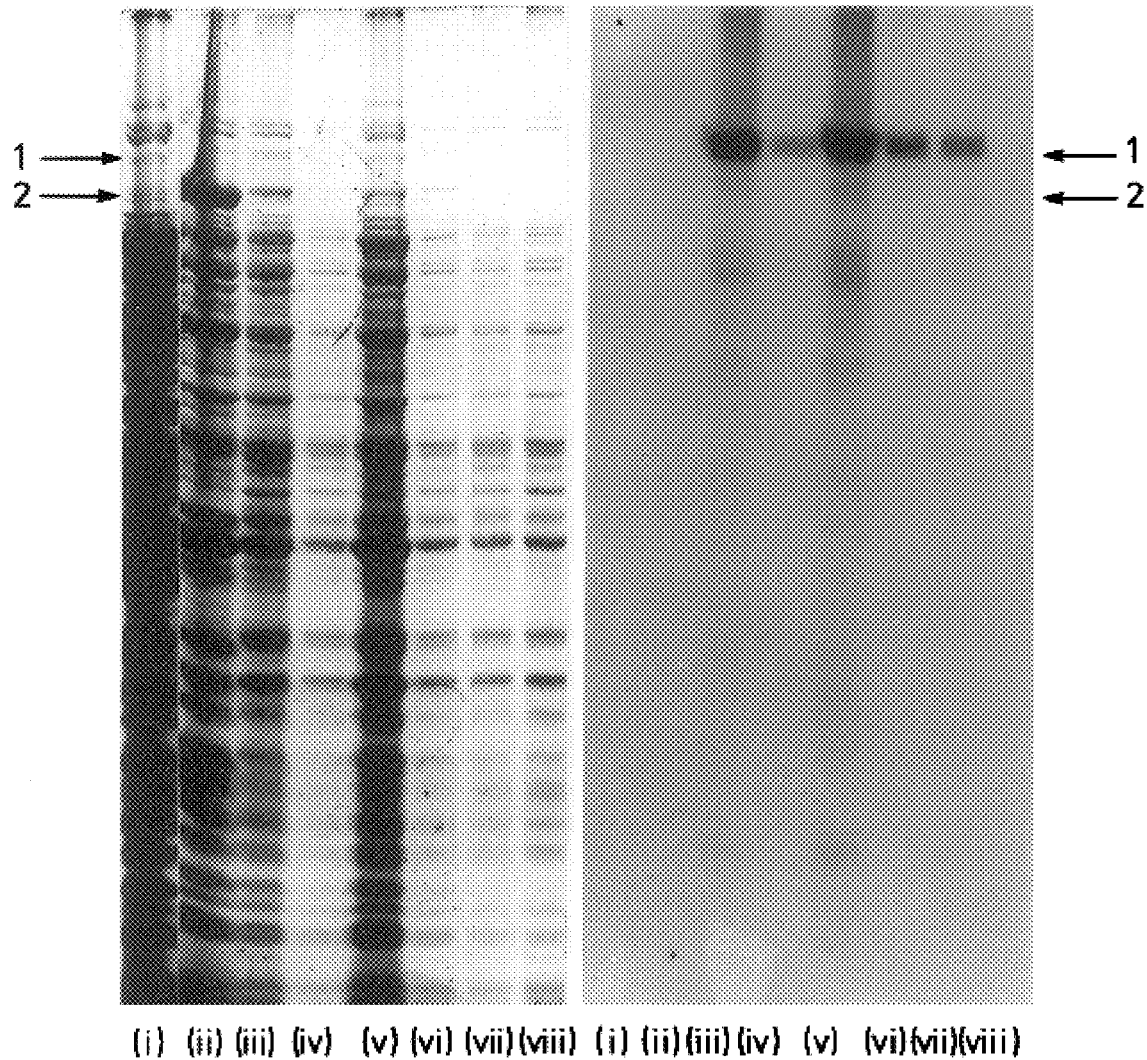

FIGS. 4A and 2B show proteins from *E.coli* colonies subjected to electrophoresis and (a) stained with Coomassie Blue, or (b) Western blotted and reacted with MAb 17-80. Arrows 1 and 2 indicate the positions of fusion protein and β-galactosidase, respectively. Samples are (i) HB 101 cells, (ii) HB 101 with pUR 290, (iii)–(viii) some recombinant clones that were identified as possible positives by reaction with MAb 17-80 (FIG. 3).

Figure 5:
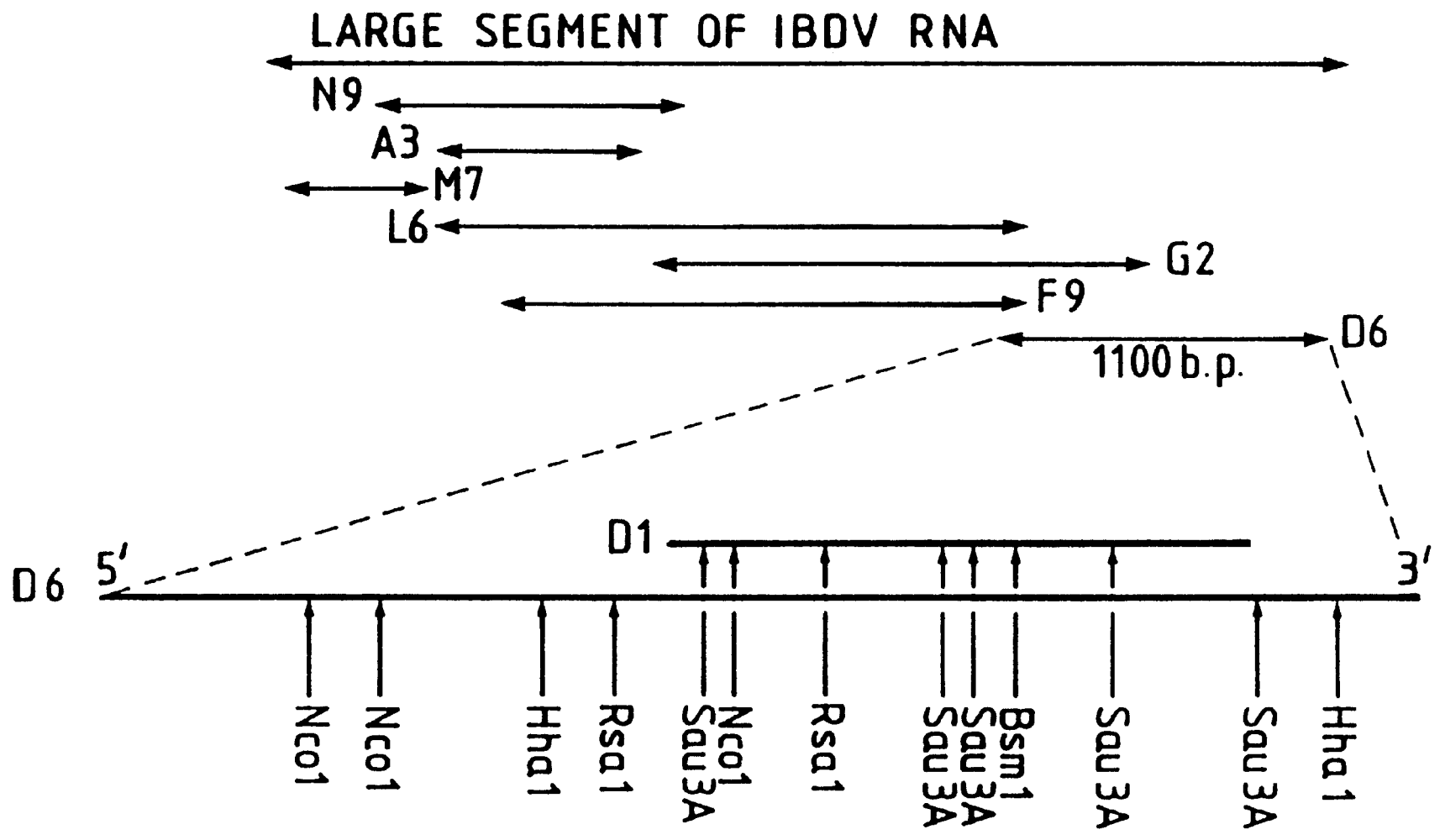

FIG. 5 shows the position of the insert from clone D6 on the large segment of IBDV genome; the restriction map of the inserts from clones D6 and D1.

Figure 6:
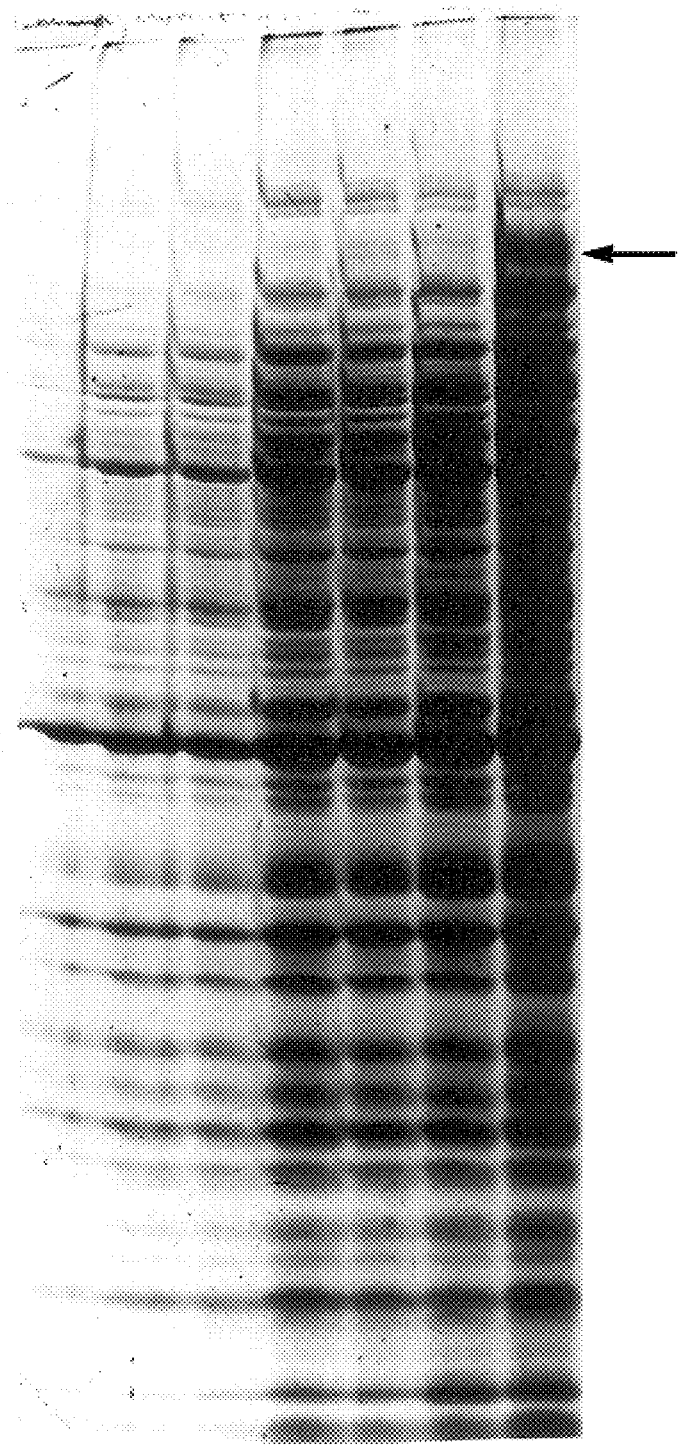
FIG. 6 shows the determination of optimum conditions for expression of fusion proteins. Cells were grown to an $O.D._{660}$ of 0.2, (i) then grown further with or without induction with 1.5 mM IPTG, (ii) 1.5 hr, (iii) 1.5 hr+IPTG. (iv) 3.0 hr, (v) 3.0 hr+IPTG, (vi) 4.0 hr, (vii) 4.0hr+IPTG. Samples were electrophoresed and the gel was stained with Coomassie blue. The arrow indicates the position of the fusion protein.

FIG. 6 shows the determination of optimum conditions for expression of fusion proteins. Cells were grown to an O.D.$_{660}$ of 0.2, (i) then grown further with or without induction with 1.5 mM IPTG, (ii) 1.5 hr, (iii) 1.5 hr+IPTG, (iv) 3.0 hr, (v) 3.0 hr+IPTG, (vi) 4.0 hr, (vii) 4.0 hr+IPTG. Samples were electrophoresed and the gel was stained with Coomassie blue. The arrow indicates the position of the fusion protein.

Figure 7:
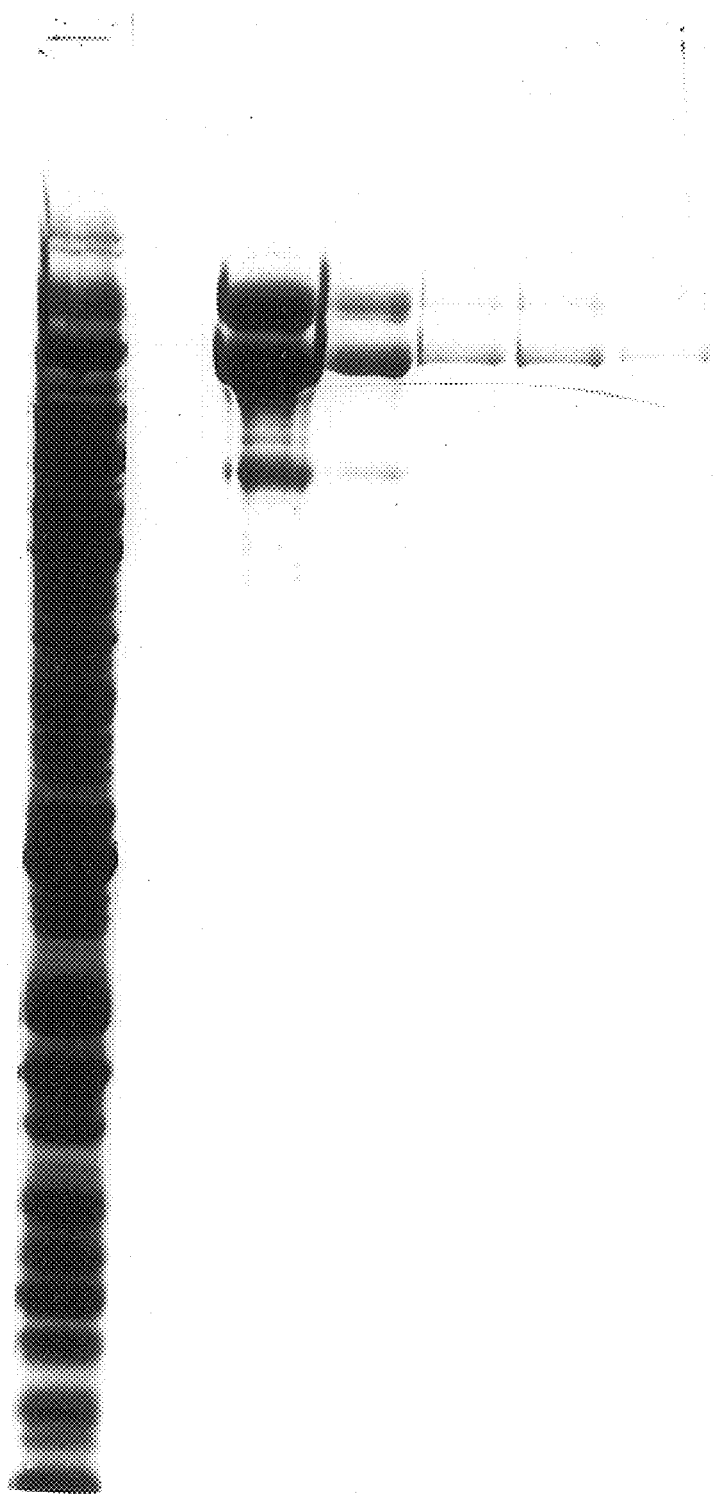
FIG. 7 shows affinity purification of fusion protein from clone D1. (i) Total E.coli protein; (ii)–(vii) fractions eluted from column.

FIG. 7 shows affinity purification of fusion protein from clone D1. (i) Total *E.coli* protein; (ii)–(vii) fractions eluted from column.

Figures 8A, 8B, 8C:
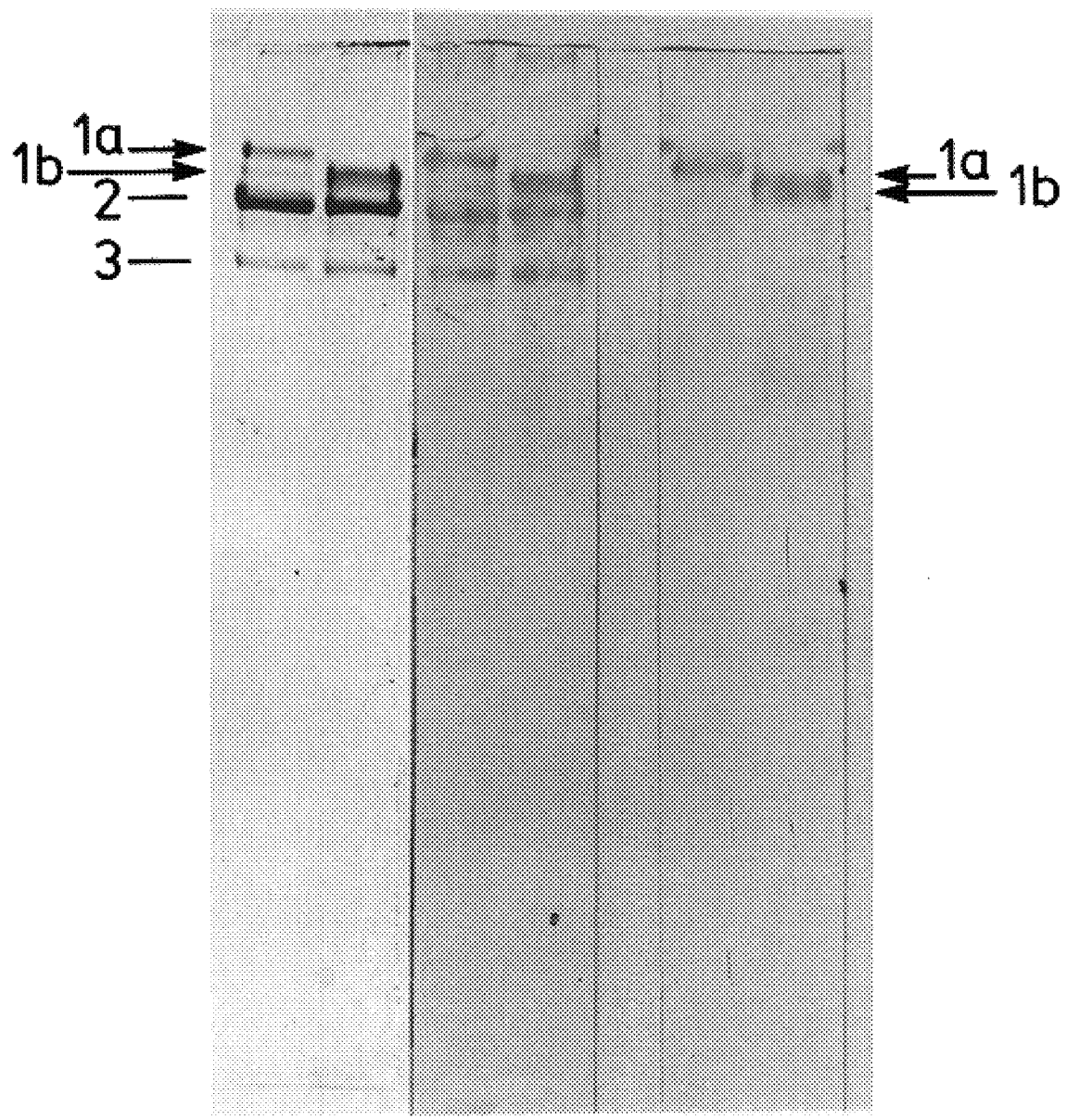
FIGS. 8A–C show affinity purified proteins from clones D1 and D6, subjected to electrophoresis and stained with Coomassie blue (a), reacted with anti-β-galactosidase (b), and reacted with anti-32Kd-monoclonal antibody (c).

FIGS. 8A–C show affinity purified proteins from clones D1 and D6, subjected to electrophoresis and stained with Coomassie blue (a), reacted with anti-β-galactosidase (b), and reacted with anti-32 Kd-monoclonal antibody (c).

Figure 9:
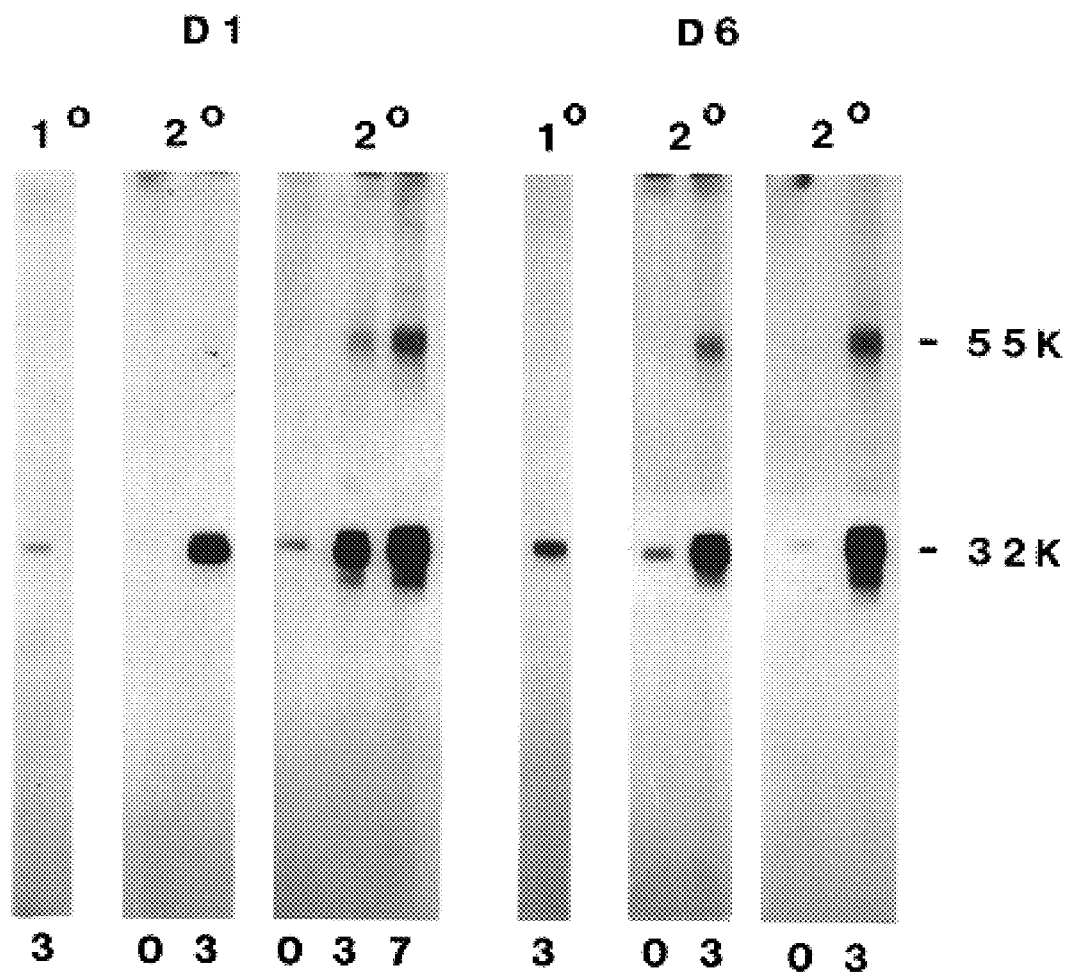
FIG. 9 shows Western blot analysis of sera from unprimed (1°) or primed (2°) chickens injected with fusion proteins from clones D1 or D6 in Freund's adjuvant. Sera obtained prior to vaccination (0), 3 weeks after injection of fusion proteins (3), or 4 weeks after a second injection of fusion proteins (7).

FIG. 9 shows Western blot analysis of sera from unprimed (1°) or primed (2°) chickens injected with fusion proteins from clones D1 or D6 in Freund's adjuvant. Sera obtained prior to vaccination (0), 3 weeks after injection of fusion proteins (3), or 4 weeks after a second injection of fusion proteins (7).

Materials and Methods

The materials and their sources are: DNase 1, lysozyme, agarose, BSA, isopropyl β-D-thiogalactoside (1 PTG) and 1-ethyl-3 (3-dimethylaminopropyl) carbodtmide (Sigma): goat anti-mouse IgG horse radish peroxidase conjugate (GAM HRP), goat anti-rabbit IgG horse radish peroxidate conjugate (GAR HRP), and HRP colour developing reagent (BioRad): α[$^{32}$P] dATP, [$^{125}$I] Protein A and Pst 1 (amersham); nitrocellulose filters and MA45 membrane filters (Schleicher and Schuell); CH-Sepharose 4B (Pharmacia): DNA polymerase (Boehringer); rabbit anti-mouse IgG (Dako immunoglobulins (Denmark). Monoclonal antibodies against IBDV were produced and characterized as described below.

IBDV strain 002-73 was grown and isolated as described earlier.

Colony and Southern blot hybridization, isolation of plasmid DNA, production of hybridization probes, agarose gel electrophoresis, polyacrylamide gel electrophoresis (Laemli) and autoradiography were performed as described earlier.

Immunoassay of Expressed Proteins in Recombinant Colonies

Recombinant colonies were grown (37°) on nitrocellulose filters on LB plates containing 30 µg/ml ampicillin. All subsequent steps were carried out at room temperature. The nitrocellulose filters were placed in a chloroform atmosphere on Whatman No. 3 paper saturated with 1% SDS for 30 minutes to 1 hour. The filters were rinsed with 50 mM Tris-HCl (pH 7.5), 150 mM NaCl (TBS) to remove cell debris, and then incubated for 1 hour with shaking in TBS containing 3% BSA, 5 mM MgCl$_2$, 1 µg/ml Dnase and 40 µg/ml lysozyme. This was followed by incubation for 1 hour in supernatant from monoclonal antibodies. The filters were then washed for 10 minutes in TBS, 10 minutes in TBS-0.1% NP40 and finally for 10 minutes in TBS. Sometimes the filters were reacted with a second antibody (rabbit anti-mouse IgG) in TBS containing 3% BSA, and washed as described earlier. Initial experiments the recombinant colonies expressing the desired protein were identified by using [$^{125}$I] Protein A. After reactions with the antibodies the filters were incubated with [$^{125}$I] Protein A in TBS containing 3% BSA. The filters were then washed for 90 minutes in 50 mM Tris-Hcl (pH 7.5), 1M NaCl, 5 mM EDTA, 0.25% gelatin, 0.4% Sarkosyl, and autoradiographed as described earlier. Tn later experiments the filters after reaction with monoclonal antibody and washing were reacted with goat anti-mouse IgG horse radish peroxidase conjugate or with goat anti-rabbit IgG horse radish peroxidase conjugate (when amplified with a second antibody) in TBS-3% BSA for 1 hour. The filters were then washed for 20 minutes in phosphate buffered saline, followed by colour development using the HRP colour developing reagent as described by BioRad.

Assay of Small Amounts of Proteins Isolated from *E.coli* Cells

*E.coli* cultures (0.8 ml in Eppendorf tubes) were grown in L broth containing ampicillin for 1–2 hours, induced with IPTG, if required, and the cells collected by centrifugation.

If the proteins were to be analyzed by polyacrylamide gel electrophoresis, the cell pellet was suspended directly in the loading buffer containing 60 mM Tris-Hcl (pH 7.5), 2% SDS, 10% glycerol, 5% β-mercaptoethanol, 0.001% bromophenol blue, and boiled for two minutes. 50 µl aliquots were loaded in duplicate on two gels. Proteins on one gel were stained with Coomassie blue, and proteins on the duplicate gel transferred to nitrocellulose filter.

For quick immunoassays of the isolated protein, the cell pellets were suspended in 300µl TBS buffer containing 40 µg/ml lysozyme (0°, 15 minutes) and then SDS was added to 1% and the solution left at room temperature for 30 minutes. Alternatively, the cell pellet was suspended in 300 µl TBS buffer and sonicated. In either case, cell debris were removed by centifigation, and 100 µl of the supernatant blotted onto nitrocellulose filter using Schleicher and Schuell Manifold apparatus. The filter was then immunoassayed as described earlier for recombinant colonies.

Western Blotting

Proteins electrophoresed on acrylamide gels were transferred to NC filters with Bio-Rad Transblot apparatus using buffers and protocol described by Bio-Rad. Proteins of interest were detected by immunoassaying the filter as described earlier.

Purification of the Expressed Fusion Protein

The fusion protein was purified by affinity chromatography (Ullmann, 1984).

Vaccination of Chicken with Fusion Proteins

Preparations of affinity purified fusion proteins D1 and D6 were emulsified in an equal volume of Freund's complete adjuvant and 1 ml injected intramuscularly into a series of adult White Leghorn chickens. The vaccines were injected into both specific pathogen free (SPF) chickens and chickens that had previously (>8 weeks) been sensitized by inoculation with live IBDV. The chickens were revaccinated three weeks later with the respective fusion proteins emulsified in Freund's incomplete adjuvant and bled at weekly intervals throughout.

Results and Discussion

1. Subcloning of cDNA Inserts into pUR Vectors:

The large segment of IBDV RNA encodes three major structural proteins including the 32 Kd host-protective antigen. cDNA inserts hybridizable to the large segment of IBDV RNA were recovered from the cDNA library by digestion of the "mixed" plasmids with Pst 1, and the "mixed" inserts were subcloned into the Pst 1 site of pUR expression vectors 290, 291 and 292, (Ruther and Muller-Hill, 1983) and these were used to transform E.coli HB101 cells. These three vectors together contain restriction sites in all three frames at the 3' end of the lacZ gene. Insertion of cDNA in the proper cloning site leads to a fusion protein of active β-galactosidase and the peptide encoded by the forein cDNA.

2. Identification of Colonies Expressing the 32 Kd Polypeptide or Parts of It

Recombinant colonies containing cDNA inserts hybridizable to the large segment of IBDV RNA were grown on nitrocellulose filters on LB plates containing ampicillin (30 μg/ml). The colonies were induced with isopropyl β-D-thiogalactopyranoside (IPTG) and then lysed by placing the filters on Whatman No. 3 paper soaked in 1% SDS in a chloroform-saturated atmosphere. After blocking with BSA, the filters were reacted with monoclonal antibodies that recognize the 32 Kd polypeptide on Western blots (MAbs17-80). The filters were then reacted with rabbit anti mouse IgG followed by [$^{125}$I] Protein A and autoradiographed. A number of possible positive clones expressing proteins that react with monoclonal antibody specific to the 32 Kd structural proteins could be seen on the autoradiograph (FIGS. 3A–3C). The protocol was modified for later experiments. After incubation with the monoclonal antibody the filter was reacted with goat anti-Mouse IgG Horse Radish Peroxidase (BioRad) and subjected to colour development.

A total of 20 possible positives were selected for further characterization. These colonies were spread on LB plates and resultant individual colonies were reprobed with monoclonal antibodies specific for the denatured 32 Kd protein. Only three of the original possible positives expressed polypeptides that reacted with the monoclonal antibody.

3. Characterization of the Expressed Proteins

The expressed proteins were characterized by polyacrylamide gel electrophoresis and Western blotting. The cells grown in Eppendorf tubes in L broth were spun down and boiled in 2% SDS for 2 minutes and loaded in duplicate on two separate gels. After electrophoresis one gel was stained with Coomassie blue, and proteins from the other gel were electroblotted onto nitrocellulose filter and probed with monoclonal antibody specific for the 32 Kd polypeptide.

Examination of the stained gel showed no prominent polypeptide band larger than β-galactosidase (FIG. 4a), but the Western blot of the duplicate samples showed very prominent polypeptide bands larger than β-galactosidase (FIG. 4b). The expressed fusion proteins from all the positive clones were of the same size, but some clones produced more of the expressed proteins than others, and this allowed us to identify clones that grew faster and expressed more of the fusion protein.

Identification of the Region of the IBDV Genome that Codes for the 32 Kd Host-protective Antigen The cDNA inserts, obtained by digestion with Pst 1, from all the positive clones were of identical size of about 450 b.p. These inserts were "nick-translated" and hybridized with a series of cDNA clones that contain a network of overlapping fragments covering the entire large segment of the IBDV genome. The inserts from the expressing clones, in every case, hybridized specifically with clone D6 which spans the 3' end of the large segment of IBDV RNA (see FIG. 5a) and other cDNA clones containing inserts of varying sizes from the same region of the IBDV genome.

The inserts from the expressing clones had identical restriction maps and were of identical size. Therefore one clone, D1, that grew well and expressed the fusion protein to a high level, was selected for further studies. The insert of D1 is present in the vector pUR 290. Comparison of the restriction maps (FIG. 5) of inserts from clones D1 (450 b.p.) and D6 (1100 b.p.) show that the D1 insert is situated towards the 3' end of the D6 insert. Sequencing studies (see later) confirm the location of the D1 insert and show that it lacks the initiation and termination codons, and constitutes about 50% of the 32 Kd host-protective antigen. The insert of clone D6 on the other hand is large enough to encode the entire 32 Kd polypeptide. Therefore, the insert from clone D6 has been subcloned in the pUR vectors and clones expressing fusion proteins larger than that from clone D1 have been obtained.

A clone containing the D6 insert in pUR vector 291 which grows well and expresses the fusion protein to a high level was selected for further studies. Clone D1 (450 b.p. insert) and clone D6 (1100 b.p. insert) both produce fusion proteins in which the C-terminal polypeptides fused to β-galactosidase react strongly with monoclonal antibodies specific for the 32 Kd host-protective antigen. Clones D1 and D6 have been used for all subsequent studies.

Optimum Conditions for Expression

The optimum conditions for the expression of the fused proteins were as follows (FIG. 6). Cells were grown in L Broth in presence of ampicillin (30 μg/ml) to an O.D. 660 of 0.2 and then induced with 1.5 mM 1PTC for 4 hours. There was no significant synthesis of the fused proteins at 3 hours after start of induction, and there was a dramatic increase in synthesis of the fused proteins after four hours of induction. Induction for longer periods or at higher cell concentrations did not result in higher yields of the fused protein.

Purification of the Fusion Proteins

The fusion proteins from clones D1 and D6 were affinity purified as described by Ullmann (1984). When pUR vectors are used for expression the β-galactosidase moiety of the fusion protein is enzymatically active and will bind to a substrate for β-galactosidase (Ullmann (1984)). E.coli cell lysate, in buffer containing 1.6M NaCl, was passed through an affinity column containing CH Sepharose coupled to p-aminophenyl-β-D-thiodalactoside and equilibrated with the same buffer. Only β-galactosidase or proteins fused to it will bind to the affinity column under these conditions. The bound protein was quantitatively eluted with 100 mM borate, pH10. The purification of fusion proteins from clone D1 is shown in FIG. 7.

The highly purified fusion proteins (D1 and D6) and free β-galactosidase (FIG. 8a) were recovered at a fairly high concentration of ca. 1–2 mg/ml, and yielded up to 20 mg of affinity purified protein per liter of culture. However, the fusion protein was subject to proteolytic degradation as evidenced by the presence of substantial amounts of polypeptides having electrophoretic mobilities similar to or faster than β-galactosidase. Three bands are seen in affinity purified proteins from clones D6 and D1. All of the bands react with anti-β-galactosidase IgG (FIG. 8b), while only bands 1a and 1b, from D6 and D1 respectively, react with the anti-32 Kd monoclonal (FIG. 8c). However, it is mainly the C-terminal IBDV protein that is substantially degraded. This degradation of the IBDV expressed protein does not seem to be caused by the isolation procedure since cells which were directly boiled in SDS prior to electrophoresis also contain substantial amounts of free β-galactosidase in addition to the intact fusion product.

Reaction of the Expressed Proteins with Monoclonal Antibodies Specific for the 32 Kd Host-protective Antigen A number of monoclonal antibodies (Mab)that recognise the 32 Kd structural protein of IBDV and/or neutralize the virus have been produced (see later). These fall into two classes. One class of Mabs (e.g.17-80) reacts with the 32 Kd proteins on Western blots but do not neutralize the virus, while the other class of Mabs (e.g.17-82) neutralize the virus but do not significantly react with the 32 Kd protein on Western blots. This suggests that the virus neutralizing monoclonal antibodies recognize a conformational epitope.

The fusion proteins expressed in clones D1 and D6 when boiled in SDS, react very strongly with monoclonal antibodies that recognize the 32 Kd structural proteins on Western blots. Both the expressed fusion proteins, when not treated with SDS, also react weakly but specifically with monoclonal antibodies that neutralize the virus. What is significant is that the IBDV polypeptide expressed in clone D1 is only 150 amino acid residues long and constitutes about half of the 32 Kd protein but contains the epitope that is recognized by the MAb that is specific for the 32 Kd protein on Western Blots (17-80), and at least a part of the epitope recognised by the MAb that neutralizes the virus (17-82).

Immunogenicity of the Expressed Proteins

Fusion Proteins from Clones D1 and D6 were injected into both SPF chickens and chickens previously sensitised with live IBDV as described under Materials and Methods. The specificity of the antibodies in the sera obtained from both groups of chickens was analysed by Western blotting of whole IBDV particles boiled in SDS prior to electrophoresis (FIG. 9).

Previously sensitized chickens had antibodies to the 32 Kd, 37 Kd and 42 Kd structural polypeptides of IBDV at relatively low levels prior to vaccination with the fusion proteins. Fusion proteins from clones D6 and D1 recalled a specific anti-32 Kd antibody response in all these chickens, while the intensity of binding to the other structural proteins remained unchanged.

In unprimed SPF chickens the fusion proteins induced the synthesis of antibodies in only some of the chickens. When antibodies were detected, however, they were specific by Western blotting for the 32 Kd structural polypeptide of IBDV. Thus the fusion proteins expressed in clones D6 and D1 induce antibodies specific for the 32 Kd polypeptide in both primed and unprimed chickens.

The sera obtained from the sensitized and SPF chickens vaccinated with the fusion proteins were assessed by the ELISA and micro-virus neutralization assays which were designed to recognize the protective immunogen in its native conformation. The levels of antibody detectable by ELISA did not increase by more than 2–4 fold above pre-existing levels in sensitized chickens or above base-line levels (<1:100) in SPF chickens, even though they reacted very strongly with Western blotted viral proteins.

The virus neutralization assay also showed no dramatic increase in the levels of antibody in previously sensitized chickens, but detected a titre of 1:320 to 1:160 in one of two SPF chickens vaccinated with affinity purified protein from clone D1. The antibody titre peaked 3 to 4 weeks after the second injection of protein from clone D1 and persisted for more than 6 weeks. By Western blotting, the polyclonal response of this chicken to D1 protein was specific for the 32 Kd polypeptide of IBDV.

Thus the antibodies produced against the fusion proteins react very specifically and strongly with Western blotted 32 Kd host-protective antiaen of IBDV, but have relatively weak ELISA titres, and virus neutralization activity in only 1 out of 4 chickens. In addition, the expressed proteins react very weakly with monoclonal antibody that neutralizes the virus. These results strongly suggest that the expressed IBDV proteins fused to β-galactosidase, though immunogenic, do not have the right conformation necessary for the consistent induction of virus neutralizing or protective antibodies. The expression of unfused proteins with the right conformation will probably be required to produce a more effective subunit vaccine against IBDV.

In this context, it should be reiterated that the serum of one chicken, injected with fusion protein from clone D1, had significant virus neutralization activity. In this instance, the IBDV protein could have been proteolytically cleaved off the β-galactosidase and assumed the conformation required for inducing virus neutralizing antibody response. In subsequent experiments, unfused 32 Kd protein has been produced by expressing the gene for the 32 Kd protein in vectors that produce unfused proteins. This unfused protein reacted with the virus neutralizing MAb 17-82, though to a lesser extent than with MAb 17-80 that preferentially reacts with denatured 32 Kd protein. Thus, one avenue for producing the 32 Kd antigen with the correct three-dimensional structure is to cleave off the IBDV antigen from affinity purified fusion protein by chemical or enzymatic cleavage at the junction of the two proteins. Although this method may require a further refolding step, the level of expression of fusion protein, in comparison to unfused protein, is very high and the fusion protein can be readily purified by affinity chromatography.

The following detailed description relates to the determination of the nucleotide sequence of the large segment of IBDV RNA and the amino acid sequence of cDNA clones that encode the 32 Kd host-protective antigen of IBDV. In the accompanying diagrams:

FIGS. 10A–10F show sequence analysis of the large RNA segment of IBDV. The predicted amino acid sequence is presented in single letter code above the nucleotide sequence derived from cDNA clones. There are no other extensive open reading frames. The amino acid sequences are numbered sequentially from the N-terminus of the 37 Kd protein as position 1. The region encompassed by cDNA clones M7, G6, L6, D6 and D1 are indicated. Dibasic residues are boxed and the repeat unit A-X-A-A-S is similarly highlighted. N-terminal sequences derived from tryptic peptides are shown overlined as (- - - ->) for the 37 Kd, (....>) for 28 Kd and (---->) for the 32 Kd protein. Only the N-terminus of the 37 Kd protein could be obtained by direct sequencing on intact proteins and this is shown from residue 1.

Results and Discussion

Random Nucleotide Sequencing

A mixed population of cDNA inserts (350–2000 bp) spanning the entire large RNA segment of IBDV was recovered on DEAE-cellulose from a 1% agarose gel after Pst 1 digestion of the selected cDNA library. After purification on a NACS column (Schleicher & Schull) the homopolymeric tails were removed using Bal 31 exonuclease in a controlled reaction (2 units, 20° C., 10 minutes) designed to digest no more than 50 nucleotides from either end. The fragments were then blunt-ended with DNA polymerase (Klenow fragment) and ligated into a Sma I restricted M13mp10 vector followed by transformation of E.coli JM101 (Sanger et.al., 1980). Single-stranded templates were sequenced by the primed synthesis method using an M13-specific primer (Sanger et.al., 1980) but with modificatons that improved transcription fidelity over regions of secondary structure in the template. These included removal of NaCl from the buffer, using reverse transcriptase and optimized ratios of dideoxy:deoxy nucleotides (1:30A; 2:15C; 1:15G; 2:3T) and performing the reaction at 30° C. or greater. Sequences were compiled using a VAX/UMS computer system using the programmes of Staden (1982) with modifications by Dr. T. Kyne.

Directed Chemical Sequencing

Specific cDNA fragments in either pBR322 or pUR expression vectors were sequenced by the Maxam and Gilbert (1977) procedure after first identifying a restriction site which could be end labelled with reverse transcriptase and either α-$^{32}$P-dATP or α-$^{32}$P-dCTP at 37° C. for one hour. This method often required a second restriction digest after the reverse transcriptase step to generate a molecule with a radiolabel at only one end. The fragments were then purified by electroelution from an 8% polyacrylamide gel. After chemical degradation the sequencing samples were loaded on denaturing polyacrylamide gels (Sanger and Coulson, 1978) which contained 90% formamide. Under these conditions when 20 cm×40 cm gels were run at 25 W on an apparatus that maintained the temperature above 50° C. the secondary structure was completely disrupted.

Nucleotide Sequence Analysis of the large RNA Segment of IBDV

Since the cDNA library was constructed with G/C homopolymeric tails of average length 20–30 nucleotides we were unable to obtain clear sequences directly over these tails by the simple subcloning of PstI fragments into M13 ventors. Instead we adopted the strategy of using Bal 31 exonuclease to remove the tails and then subdlone random cDNA fragments of the IBDV genome by blunt-end ligation into Sma I digested M13mp10. The cDNA fragments were initially selected as having originated from the large RNA segment by colony hybridization with a specific probe. Random nucleotide sequences were rapidly sorted and overlapped into a consensus sequence with the aid of computer programmes. The final alignment comprised 2950 bp and was constructed from over 60 overlapping sequences. No point mutations or rearrangements were found in the overlapping sequences which confirms that the original library construction by randomly primed transcripts followed by reannealing and polymerase elongation was remarkably error-free.

However, two problems emerged with this approach. Firstly the subcloning was definitely not random; some regions were sequenced many times whereas cDNA fragments containing the region from nucleotides 2250–2600 could not be subcloned into M13. Secondly the general quality of nucleotide sequence obtained by the chain termination method of Sanger et.al. (1980) was poor due to multiple regions of secondary structure causing premature terminations in the transcriptase reaction. This latter problem was partly overcome by the use of reverse transcriptase under optimized conditions rather than the standard DNA polymerase (Klenow fragment). These secondary structure problems appear to be particularly severe for this double stranded RNA virus since other genes being sequenced at the same time (Hudson et.al., 1984; McIntyre et.al., 1985). To overcome these problems we resorted to the chemical degradation technique of Maxam and Gilbert (1977) which is less affected by secondary structure and the use of denaturing formamide gels to resolve the sequencing ladder. Interestingly, the region with the most severe secondary structure problems (nucleotides 2540–2565) was contained within the fragment which could not be subcloned into M13. The significance of this structure which is lethal to M13 has not been further characterized; it is contained within the coding region of the 32 Kd protein product.

Identification of the Gene Encoding the 32 Kd Host-protective Immunogen

Two methods were attempted in parallel; protein sequencing of tryptic peptides derived from purified 32 Kd protein and identification by immunoblot assay of cDNA clones expressing fragments of the 32 Kd antigen as a fusion protein. For the expression studies vectors have recently been described in which cDNA fragments can be ligated into the 3'end of the β-galactosidase gene (Ruther and Muller-Hill, 1983; Stanley and Luzio 1984). The fusion proteins produced by these constructions appear to be particularly stable and has lead to claims of hybrid-protein synthesis up to 30% of the host cell proteins. With suitable inducible promoters sufficient protein is produced to form amorphous aggregates appearing as inclusion bodies. Plasmid vectors which have been designed to express only the gene encoded by the cDNA (pUC, pCQV) do not appear to produce such high levels of expressed protein. For these reaons we chose to subclone a mixed population of cDNA fragments spanning the entire IBDV genome, still containing homopolymeric tails, into the Pst I site of vectors pUR290, pUR291, pUR292 to ensure translation in all three reading frames. Recombinant colonies were screened by an immunoblot assay using a monoclonal antisera raised against denatured 32 Kd protein (see later) followed either by autoradiography using $^{125}$I-protein A or visible detection by a peroxidase conjugated second antisera. Two colonies expressed the epitope recognised by the anti-32 Kd antisera; one was a direct subclone of the 1100 bp fragment D6 described previously, and the other a shorter 450 bp cDNA fragment D1 entirely contained within D6 (FIG. 10A–10F).

Directed nucleotide sequencing over the homopolymeric tails from the EcoRI site in the pUR vector readily identified both the cloning vector (pUR290 for D1; pUR291 for D6 and the translation phase of the recombinant product. The entire nucleotide sequence of D6 and D1 was obtained by the Maxam and Gilbert technique on suitable end-labelled fragments. This sequence overlapped the consensus generated by the random sequencing approach, thus spanning the region which could not be subcloned into M13 and completing the 3129 bp genome presented in FIG. 10.

With the exception of the D6 region the rest of the genomic sequence had been compiled from multiple independent cDNA clones. Although this random approach showed that the original construction of the cDNA library was remarkably error-free we were concerned that regions with secondary structure in D6 could have been transcribed incorrectly. To settle this point two further clones (G2 and N1) spanning residues 1250–2750 and 2210–3150 respectively were sequenced completely by the direct chemical method. No ambiguities were found between D6 and these clones indicating that the transcription of the IBDV genome was correct. The only differences observed between any cDNA clones were always located in the last ten nucleotides adjacent to the homopolymeric tails. These sequences are known to contain potential errors generated by the DNA polymerase fill-in reaction (Hudson et.al., 1984) and were therefore not included in the consensus. Any areas of potential ambiguity due to secondary structure affecting the random sequencing approach were resolved by direct chemical sequencing from a suitable restriction site within the cDNA inserts of M7, A3, L6, G2 or D6 which together span the entire sequence presented in FIG. 10.

The 5' and 3' terminal sequences of the consensus are defined by the ends of M7 and D6 respectively.

Structure of the 32 Kd Antigen

On FIGS. 10A–10F arrows indicate the translational phase in the pUR subclones of D6 and D1 bearing in mind that the initial residue adjacent to the homopolymeric tails has not been included. Although the termination codon at residue 3065 is unambiguous, the N-terminal residue of the 32 K antigen is not clear. If the protein is generated from a polycistronic RNA template as implicated for the related IPNV or Drosphilaxviruses we would expect initiation at MET 2287 giving rise to a product of 29 Kd which is consistent from size estimates. However if the 32 Kd protein is generated by processing of a precursor we might expect proteolytic cleavage somewhere before the MET residues, assuming the C-terminus is intact.

Peptide sequencing of tryptic fragments has confirmed both the reading phase predicted from the D6 and D1 expression vectors and that the 32 Kd protein spans residues 2372–3008. All nine peptides sequenced to date are located from the region 3' to MET 2287. However, the intact 32 Kd antigen has a blocked N-terminus which perhaps suggests Gln 2274 as the N-terminal residue after proteolysis.

The amino acid sequence derived from the complete nucleotide sequence of the large segment of the IBDV genome is shown in FIG. 10A–10F. Partial peptide sequencing of purified viral proteins has confirmed these sequences and allowed the positioning of the coding regions of the viral proteins on the large segment of the genome. There is only one translation termination codon at the 3' end of the genomic RNA, and it would appear that the entire genome is expressed as a single polyprotein in which the viral proteins are arranged in the following order: N-41/37 Kd -28 Kd -32 Kd-C. The exact processing mechanism of this large precursor to the viral proteins has not yet been defined. Dibasic residues, which are frequent targets for eukaryotic precursor proteins, are conveniently situated at residues 451–452 and 721–722 and cleavage at these sites would excise a predicted 28.2 Kd protein. The cleavage sites are consistent with peptide sequencing data which confirms that the 37 Kd protein spans at least base residues 32–1310, the 28 Kd protein at least base residues 1660–1870, and the 32 Kd protein at least base residues 2310–3030. The region encoding the 37 Kd protein is also expected to encode the larger 52 Kd and 41 Kd precursors of the 37 Kd protein. An alternative cleavage site could be the peptide sequence A-X-A-A-S which is repeated three times between residues 483–503 and also appears at residues 752–756.

Figure 11:
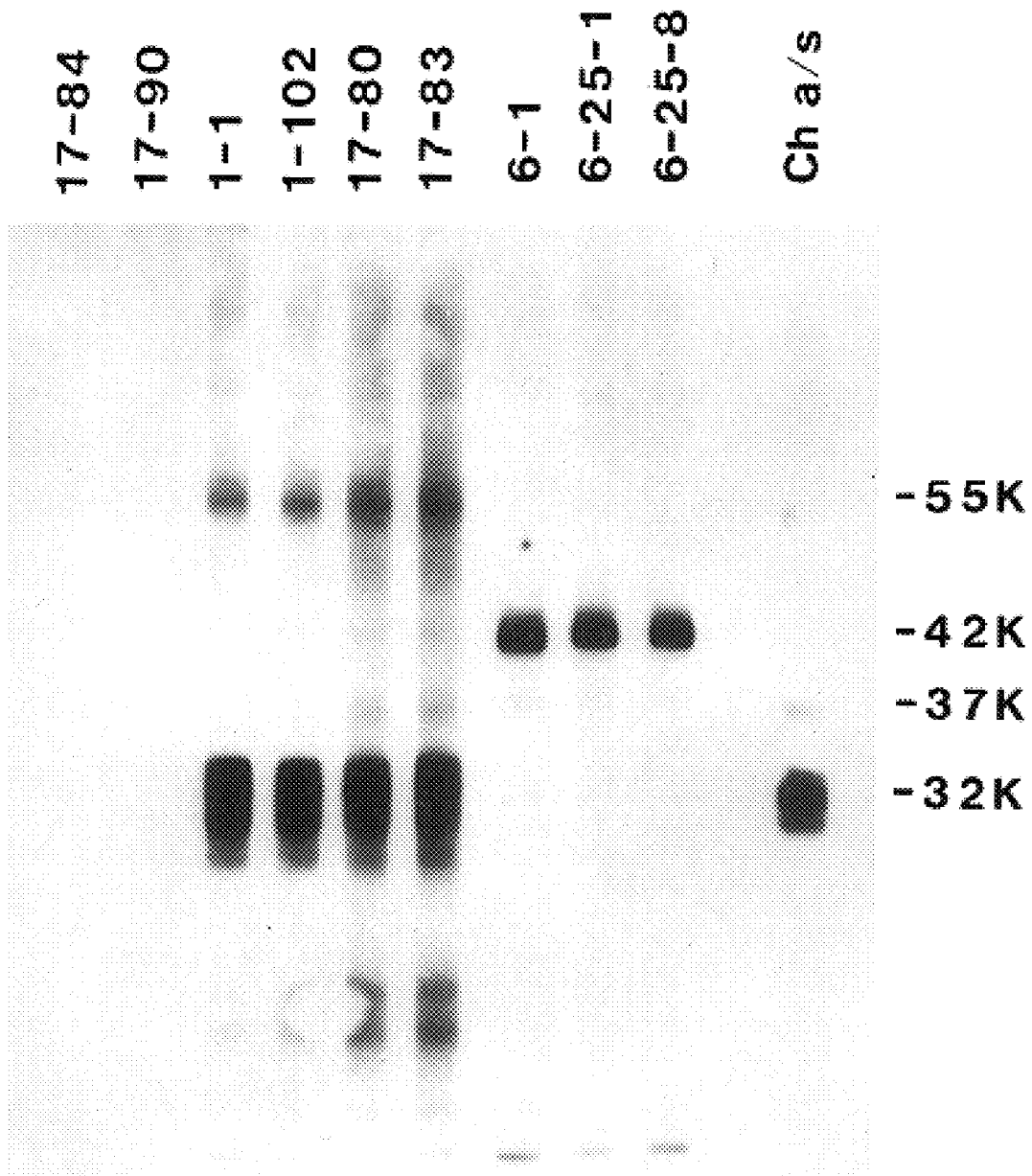
FIG. 11 shows Western blot analysis of anti-IBDV Mabs against whole virus following SDS-PAGE.

The following detailed description relates to the production of monoclonal antibodies (MAbs) to IBDV and to the identification of a neutralising epitope on IBDV using these monoclonal antibodies. In the accompanying diagrams:

FIG. 11 shows Western blot analysis of anti-IBDV MAbs against whole virus following SDS-PAGE.

Figure 12A:
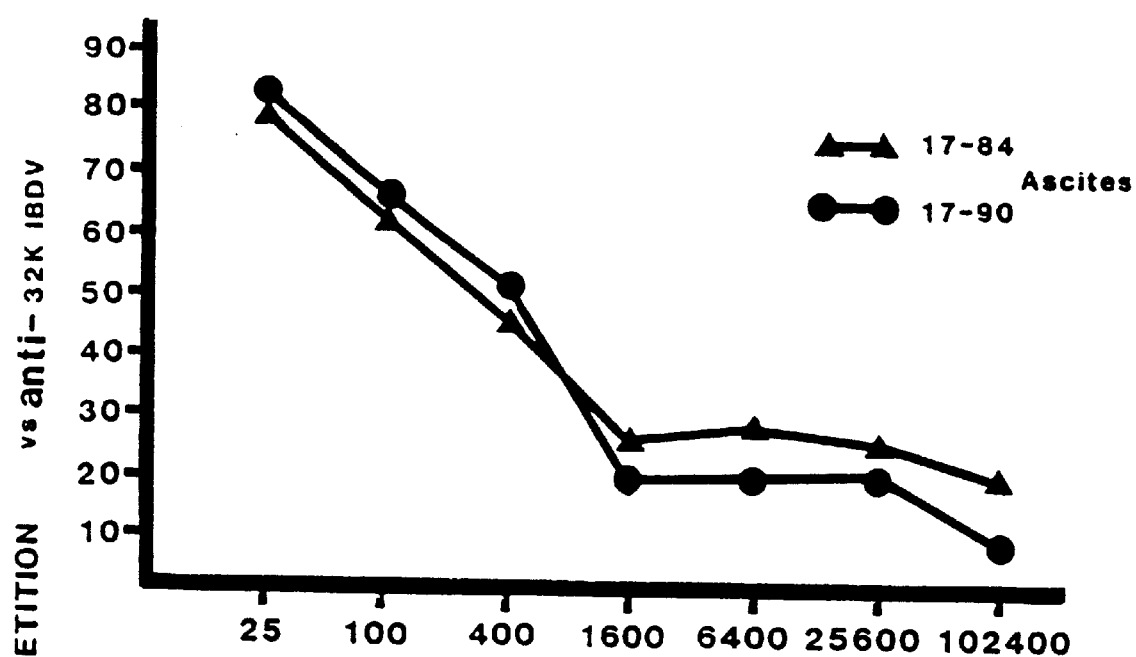
FIGS. 12A and 12B show competitive ELISA between anti-IBDV Mabs and a chicken anti-32Kd specific antisera to IBDV.

FIGS. 12A and 2B show competitive ELISA between anti-IBDV MAbs and a chicken anti-32 Kd specific antisera to IBDV.

Results and Discussion

Mouse monoclonal antibodies (Mabs) to IBD virus were prepared by hyper-immunising Balb/C mice with purified virus and fusing the immune spleen cells with SP2/0 myeloma cells according to the method of Hewish et.al (1984). Antibody secreting colonies were detected by an Immunodot assay (Bio Rad) on whole virus and by the IBD virus ELISA described in International Patent Specification No. PCT/AU84/00256, modified to detect mouse antibodies by using goat anti-mouse Ig-HRP (Bio Rad). The positive colonies were cloned by limiting dilution on at least 3 occasions, selecting positive colonies by the above assays at each cloning.

The specificity of the MAbs was assessed by Western blotting whole virus (Patent Specification No. PCT/AU84/00256) again modified to detect mouse antibodies by using rabbit anti-mouse Ig (Sera-lab). The majority of MAbs were specific for the 32 Kd structural polypeptides of IBD virus, as exemplified by the series 1 and 17 MAbs shown in FIG. 11. Only one series of MAbs, series 6, recognised the 42 Kd polypeptide (FIG. 11) and none have yet been obtained that specifically react with the 37 Kd polypeptide. A subclone of the series 17 MAbs, designated 17-82, did not bind to SDS denatured IBD viral polypeptides (FIG. 11). All the MAbs that were positive for viral polypeptides on Western blots also bound to material on the blots that were of lower mol. wt. than any of the known structural proteins of IBD virus (Dobos, 1979; Patent Specification No. PCT/AU84/00256) and may therefore represent degraded viral proteins. The anti-32 Kd monoclones, particularly of the 17-80 and 17-83 lineage bound to a large molecule which had an approximate mol. wt. of 55 Kd and may represent the unprocessed precursor molecule described earlier.

The relative antibody activity of the MAbs was assessed by the ELISA and the Immunodot assay; the latter on both denatured and nondenatured virus (Table 1). Ascites fluid from mice inoculated with myeloma cells of the series 1 and 17 all had high titres of antibodies by the ELISA and Immunodot assays ($2\_^{14}2^{19}$) performed on native virus, although the Immunodot reactivity of the 17-82 lines was abolished by treatment of the virus with SDS and boiling. The series 6 MAbs reacted weakly in both assays (Table 1), although this time the reactivity of the MAbs in the Immunodot assay was enhanced by treating the virus with SDS and boiling.

TABLE 1

Summary of the specificity, relative activity and isotypes of the MAbs to IBD virus.

| | AB Specificity | | AB Activity | | | | |
| | | | | Virus | | | AB |
| | Western | Competi- | | Immunodot | | Neutral- | Iso- |
| MAb | blot | ive ELISA | ELISA | −SDS | +SDS | isation | type |
|---|---|---|---|---|---|---|---|
| 1 | 32 Kd | ? | ++++ | +++ | +++ | − | $G_1$ |
| 6 | 42 Kd | ? | + | + | +++ | − | $G_1$ |
| 17–80 | 32 Kd | ? | +++ | +++ | ++++ | − | $G_1$ |
| 17–82 | ? | 32 Kd | ++++ | ++++ | − | ++++ | $G_{2b}$ |

When the virus neutralizing activity of the MAbs was assessed in the micro-virus neutralization assay (Patent Specification No. PCT/AU84/00256) only the MAbs of the 17-82 lineage neutralized the infectivity of the virus; the ascites fluid having a titre of $2^{14}$. MAbs of the series 1 and 6 and of the 17-80 lineage were all negative ($<2^4$).

Figure 12B:
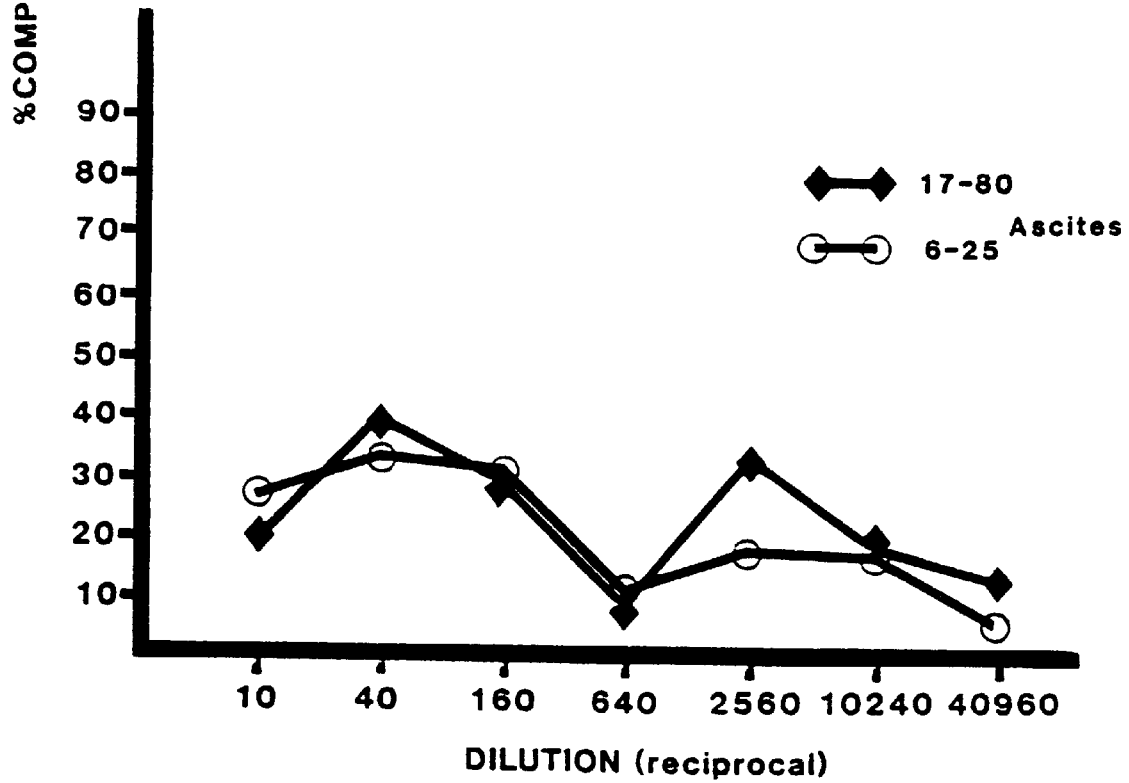

The specificity of the 17-82 MAbs was investigated in a competitive inhibition ELISA against chicken antisera specific for the 32 Kd polypeptide of IBD virus by Western blotting. The 17-82 MAbs effectively competed out the chicken anti-32 Kd antibodies (FIG. 12), while the 17-80 and series 6 MAbs were much less effective (FIG. 12). The 17-82 MAbs also completed out a polyspecific chicken antisera, which recognized the 32 Kd, 37 Kd and 42 Kd viral polypeptides on Western blots (data not shown), indicating that the 17-82 MAbs were against a dominant immunogen on the virus.

The isotype of the anti-IBD virus MAbs was determined by an ELISA utilising either anti-mouse lambda chain, IgM, IgG1, IgG2a+2b, IgG2b or IgG3 as the second step reagent. All blAbs were of the mouse IgG1 class except the 17-82 line MAbs, which were of the IgG2b class.

The series 6 MAbs were of particular interest as we believe from HPLC analysis of a tryptic and chrymotryptic digest of the 37 Kd and 42 Kd polypeptides that the latter is the precursor of the former. It would seem likely therefore that the series 6 MAbs recognise the peptide sequence cleaved off during the formation of the major 37 Kd structural polypeptide of the Australian type-1 IBD virus.

Because of their ability to recognise SDS denatured 32 Kd polypeptide of IBD virus, MAbs of the 17-80 lineage were used to select recombinant bacterial colonies expressing part or all of the 32 Kd polypeptides as described above.

Figure 13:
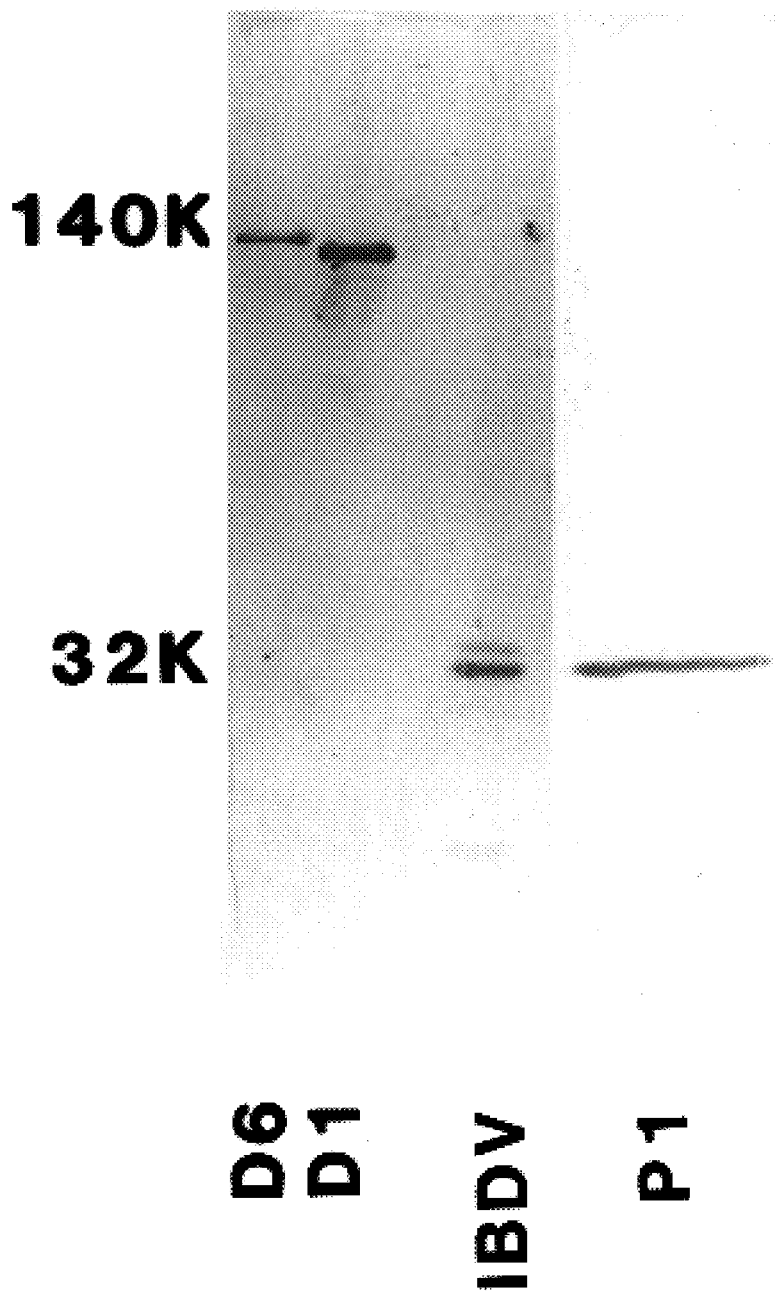
FIG. 13 shows proteins expressed in clones D6, D1 and P1, and IBDV proteins, which were Western blotted and reacted with Mab 17–80. The insert of clone P1 was constructed by ligating the L6 and D6 inserts via the Apa I restriction site to retain the exact genomic sequence of native IBDV over this region.

The following detailed description relates to the production of the 32 Kd structural protein in its unfused form. In the accompanying diagrams:

FIG. 13 shows proteins expressed in clones D6, D1 and P1, and IBDV proteins, which were Western blotted and reacted with MAb 17-80. The insert of clone P1 was constructed by ligating the L6 and D6 inserts via the Apa I restriction site to retain the exact genomic sequence of native IBDV over this region.

Figure 14:
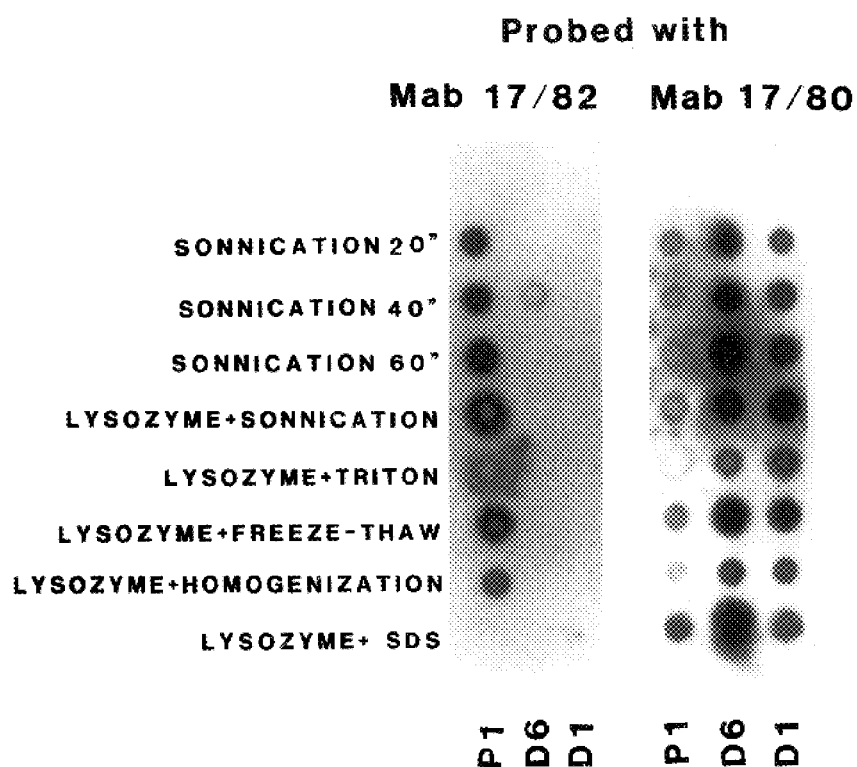
FIG. 14 shows clones D1, D6, and P1 which were lysed by various treatments and the proteins blotted onto nitrocellulose filters, then reacted with either Mab 17–80 or Mab 17–82. The expressed proteins were visualised by reaction with [$^{125}$I] Protein A followed by autoradiography.

FIG. 14 shows clones D1, D6 and P1 which were lysed by various treatments and the proteins blotted onto nitrocellulose filters, then reacted with either MAb 17-80 or MAb 17-82. The expressed proteins were visualised by reaction with [$^{125}$I] Protein A followed by autoradiography.

Figure 15:
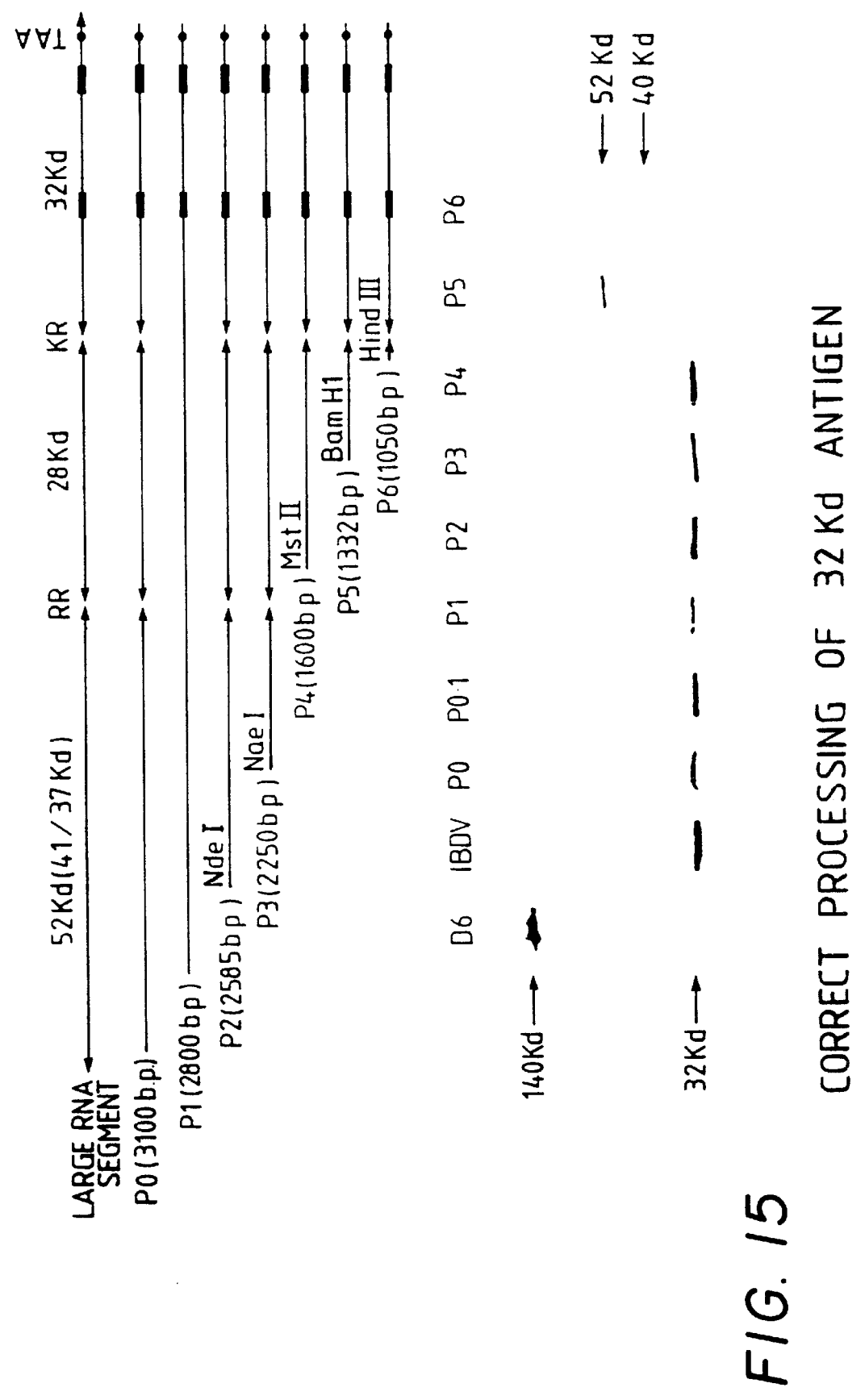

FIG. 15 indicates the minimum size of precursor polypeptide that has to be expressed for the correct processing of the 32 Kd antigen. The insert of clone PO, that contains the entire coding region of the large segment of IBDV genome, was progressively shortened at the 5' end at specific restriction sites and the resultant fragments were expressed in pPL vector in *E.coli*. Expressed gene products were Western blotted and reacted with MAb 17-80.

Figure 16:
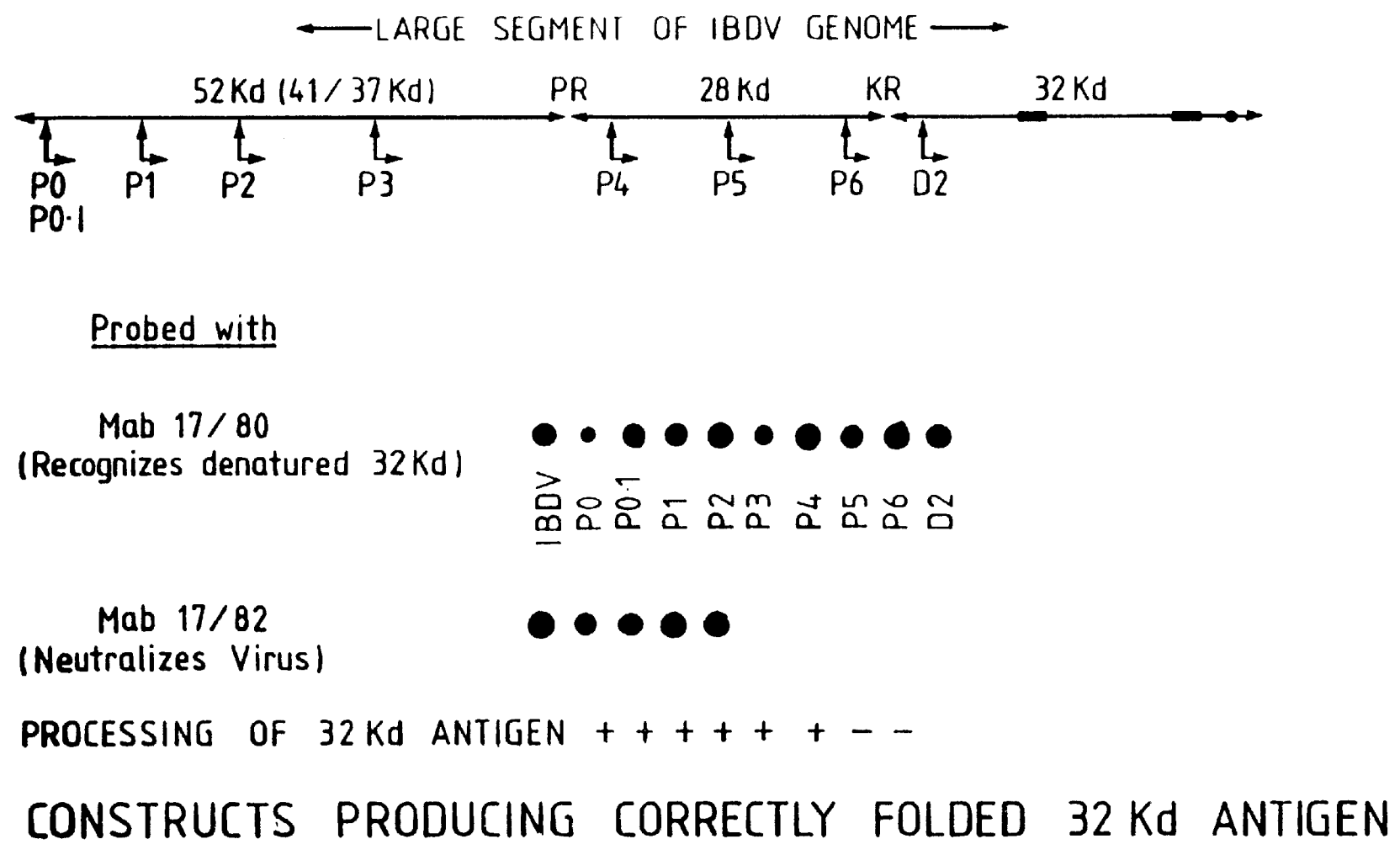

FIG. 16 indicates the regions of the precursor polypeptide that may contribute to the antigenic determinant recognised by the virus neutralising monoclonal MAb 17-82. Undenatured proteins from clones containing precursors of varying sizes were blotted onto nitrocellulose filter and reacted with MAb 17-80 or MAb 17-82.

A large recombinant molecule spanning bases 425-3145 was constructed by joining the inserts of clone D6 (which encodes the 32 Kd protein) and clone L6 (which encodes the 28 Kd protein and the major part of the 41/37 Kd protein)—full details of both these clones are set out above. L6 and D6 inserts were ligated via the Apa I restriction site to retain the exact genomic sequence of native IBDV over this region. This large recombinant molecule (PI) was expressed in pUR plasmids in *E.coli* and the expressed protein analysed by Western blotting and reaction with MAb 17-80 (FIG. 13). The large insert was expected to express a viral polyprotein of M>80 Kd (or ~190 Kd as a fusion protein) but instead produced a discrete 32 Kd protein that specifically reacted with MAb 17-80.

To see if the correct processing of the expressed polypeptides leads to their being correctly folded the proteins expressed in clone P1 were analysed by an immunoblot assay (FIG. 14) using a monoclonal antibody (Mab 17-82) that neutralises the virus but does not react with denatured 32 Kd viral protein. The expressed proteins reacted quite strongly with MAb 17-82, but this reaction was completely abolished when the expressed protein is first denatured in SDS. After denaturation in SDS, the expressed protein reacted strongly with MAb 17-80 which recognises denatured 32 Kd protein. Thus, the genetically engineered polypeptides mimic the immune response of the whole virus particle towards MAb 17-82 and MAb 17-80.

These results clearly demonstrate that the expression of a large cDNA fragment encoding the 32 Kd protein, the 28 Kd protein and a major portion of the 41/37 Kd protein results in the synthesis of an unfused 32 Kd protein that is recognised by a monoclonal antibody (Mab 17-80) which reacts with denatured 32 Kd host-protective antigens of IBDV. Tn the "native" form, the genetically engineered polypeptides react specifically with the virus neutralising monoclonal antibody (Mab 17-82) suggesting that they may be folded in the same conformation as the native viral antigen.

A larger recombinant molecule (P0) containing the entire coding region of the large RNA segment of IBDV was constructed by ligating the insert of clone P1 to the insert of another clone G6 through a common Nde1 restriction site. P0 was expressed in pEX vector (Stanley and Luzio, (1984)), in *E.coli*. As in the case of P1, this resulted in the production of a correctly processed 32 Kd polypeptide that reacted with MAb 17-80.

The 32 Kd protein produced in clones P1 and P0 might be processed by a virus-specified protease. Alternatively, a translation initiation site recognised by *E.coli* ribosomes may be present within or just before the gene for the 32 Kd protein. If this is the case then the introduction of frame shifts within the 28 Kd protein should not affect the production of the 32 Kd polypeptide in clone P0. Frame shifts were introduced by inserting the 1.3 Kb Km$^R$ fragment (Vieira and Messing (1982)) into the EcoR1 or Bam H1 sites within the gene for the 28 Kd protein, or by deleting the EcoR1—Bam H1 fragment. In none of these instances was a 32 Kd or higher MW protein produced that reacted with MAb 17-80 on Western blots. This ruled out the possibility that the 32 Kd protein is expressed from an independent translation initiation site.

In order to localize the putative virus-specified protease the insert from clone P0 was progressively shortened from the 5' end at specific restriction sites (FIG. 15) and resultant fragments of different sizes were inserted into vectors that produced either fusion proteins or unfused proteins, and the same results were obtained irrespective of the type of vector used. The proteins expressed in *E.coli* were Western blotted and reacted with MAb 17-80 (FIG. 15) to see how much of the coding sequence besides the 32 Kd polypeptide has to be expressed in order to produce the correctly processed 32 Kd protein. FIG. 15 shows the results obtained by expression in a fusion vector (pPL) that adds on about 7 Kd of the XN gene product to the expressed protein.

The deletion of part or whole of the gene coding for the 52 Kd precursor of the 37 Kd protein or the N-terminal portion of the 28 Kd protein did not in any way interfere with the production of the 32 Kd polypeptide. However, the removal of further portions of the gene encoding the 28 Kd protein (Bam H1 and Hind III restriction sites) inhibited the processing of the 32 Kd protein even though the dibasic residues at the approximate junction between the 32 Kd and 28 Kd proteins were still present. Similar results were obtained by site-specific insertional mutagenesis studies using Km cassettes (Vieria and Messing, (1982)). Insertion of 10 codons 'in-phase' into the EcoR1 site near the 5' end of the 28 Kd protein does not affect the production of the correctly processed 32 Kd protein, whereas the insertion 'in-phase' of 4 codons into the Bam H1 site in the middle of the 28 Kd protein inhibits the processing of the 32 Kd protein and a much large precursor molecule is produced.

These results together with the fact that the 28 Kd protein is present in very minute and variable quantities in the mature virus particle would suggest that the 28 Kd protein is an IBDV specific protease involved in the processing of the large precursor polypeptide.

The proteins expressed in clones P1 and P0 react strongly with the virus neutralizing MAb 17-82. Since clones P1 and P0 produce correctly processed 32 Kd protein and other proteins encoded by the large segment it was important to know whether the correct processing of the proteins resulting from the expression of large precursor molecules leads to the expressed polypeptides assuming the correct 3-dimensional structure that is recognised by the virus neutralizing MAb 17-82. Recombinant molecules of various sizes containing the gene for the 32 Kd protein and part or whole of the gene(s) for the 28 Kd and 52 Kd proteins, were expressed in *E.coli*. The undenatured expressed proteins were blotted onto nitrocellulose filter and reacted with MAb 17-80 or MAb 17-82 (FIG. 16). While MAb 17-80 reacted with proteins expressed in all the constructs, the virus neutralizing MAb 17-82 only reacted with proteins expressed in clones in which the substantial portion of the 52 Kd precursor of the 37 Kd protein is retained (FIG. 16). On the other hand, FIG. 15 clearly shows that the correct processing of the 32 Kd protein does not require any portion of the 52 Kd protein or even the extreme N-terminal portion of the 28 Kd protein. Thus the correct processing of the 32 Kd protein alone does not ensure recognition by MAb 17-82, and a portion of the 52 Kd precursor protein may be directly or indirectly involved in the process.

The antigenic determinant recognised by the virus neutralizing MAb 17-82 may consist of a discontinuous epitope made up of contributing regions from both the 32 Kd and 41/37 Kd proteins. Fusion proteins from clones D6 and D1 in the undenatured state, react weakly, but quite specifically with virus neutralising MAb 17-82. Unfused protein produced by the expression of the Aha II-Pst 1 fragment of the 32 Kd gene, also react with MAb 17-82. Thus the 32 Kd protein or part thereof, is recognised albeit weakly by MAb 17-82. In order to see if MAb 17-82 also reacted with the 52 Kd precursor protein of the 41 and 37 Kd structural proteins, the gene encoding this region, without those genes coding for the 28 Kd and 32 Kd structural proteins, was expressed in pEX vector in *E.coli*. The undenatured expressed protein reacted strongly with MAb 17-82, indicating that the 52 Kd precursor also contained an epitope(s) recognised by the virus neutralising MAb. It is possible that an interaction between the 32 Kd and the 41/37 Kd structural proteins may be involved in formation of epitope(s) that induce virus neutralising and/or protective antibody.

Thus one viable approach to producing the correctly processed and folded antigens is to express the entire coding region or precursors retaining the 32 Kd, 28 Kd and a substantial portion of the 52 Kd precursor proteins. The antigens produced by this method can be readily purified by affinity chromatography using monoclonal antibodies, or by engineering specific sequences at the termini of the expressed antigens.

Another approach is to express the complete gene or fragments thereof for the 32 Kd and/or the 52 Kd protein. A susbsequent refolding step may or may not be required. This approach is quite feasible since we have previously demonstrated (International Patent Application PCT/AU84/00256) that the viral 32 Kd protein isolated from SDS-polyacrylamide gel can refold and when injected into chickens produce virus neutralizing and protective antibodies. Moreover, an unfused protein of 30 Kd produced by the expression of the AhaII-Pst 1 fragment of the 32 Kd gene in pCAV2 vector reacts with the virus neutralizing MAb 17-82. The protein expressed from the gene for the 52 Kd precursor of the 41 Kd and 37 Kd structural proteins also reacts with the virus neutralising MAb 17-82.

A third approach to producing the viral antigen in *E.coli* is to produce fusion proteins in which an enzymic or chemical cleavage site has been engineered at the junction between the IBDV and host proteins. The levels of expression of fusion proteins are very high and the expressed protein can be readily purified by affinity chromatography. The IBDV protein can be recovered by enzymic or chemical cleavage of the purified fusion protein.

REFERENCES

1. BIRNBOIM, H. D., and DOLY, J. (1979) Nucl. Acids Res. 7, 1513–1523.
2. BLAKE, A. and PEACOCKE, A. R. (1968). Biopolymers 6, 1225–1253.
3. DIAZ-RUIZ, J. R., and KAPER, J. M. (1978). Prep. Biochem. 8, 1–17.
4. DOBOS, P. (1979). *J. Virology*, 32, 1046–1050.
5. FIRTH, G. A., (1974). Aust. Vet. J. 50. 128–130.
6. GOLDBACH, R. W., BORST, P., BOLLEN-DE BOER, J. E., and VAN BRUGGEN, E. F. J. (1978). Biochem, Biophys. Acta 521, 169–186.
7. GRUNSTEIN, M. and HOGNESS, D. S. (1975). Proc. Natl. Acad. Sci. USA 72, 3961–3965.
8. HEWISH, D. R., ROBINSON, C. P. and SPARROW, L. G. (1984). Aust.J.Biol.Sci., 37, 17–23.
9. HUDSON, P., JOHN, M., CRAWFORD, R., HARALAMBIDIS, J., SCANLON, D., GORMAN, J., TREGEAR, G., SHINE, J., and NIALL, H. (1984) EMBO J. 3, 2333–2339.
10. ISH-HOROWICZ, D., and BURKE, J. F. (1981). Nucl. Acids Res. 9, 2989–2998.
11. LERMAN, L. S. (1963). Proc. Natl. Acad. Sci. USA 49, 94–102.
12. MARGLIN, A., and MERRIFIELD, R. B. (1970) Auno. Rev. Biochem., 39, 841.
13. MAXAM, A. M. and GILBERT, W. (1977) Proc. Natl. Acad. Sci. 74, 5463–5467.
14. McINTYRE, P., GRAF, L., MERCER, J., WAKE, S., HUDSON, P. and HOOGENRAAD, N. (1985) DNA 4, in press.
15. MULLER, H., SCHOLTISSEK, C. and BECHT, H. (1979). J. Virol. 31, 584–589.
16. RIGBY, P. W. J., DIECKMANN, M., RHODES, C., and BERG, P. (1977). J. Mol. Biol. 113, 237–251.
17. RIXON, F., TAYLOR, P., and DESSELBERGER, U. (1984). J. Gen. Virol. 65, 233–239.
18. RUTHER, U. and MULLER-HILL, B. (1983) EMBO J. 2, 1791–1794.
19. SANGER, F., COULSON, A. R., BARRELL, B. G., SMITH, A. J. H. and ROE, B. A. (1980) J. Molec. Biol. 143, 161–178.
20. SANGER, F. and COULSON, A. R. (1978) FEBS Lett. 87, 107–110.
21. STADEN, R. Nucleic Acids Res. (1982) 10, 4731–4751.
22. STANLEY, K. K. and LUZIO, J. P. (1984) EMBO J. 3, 1429–1434.
23. TAYLOR, J. M., ILLMENSEE, R., and SUMMERS, J. (1976). Biochem. Biophys. Acta 442, 324–330.
24. TODD, D., and McNULTY, M. S. (1979). Arch. Virol. 60, 265–277.
25. ULLMANN, A. (1984). Gene. 29, 27–31.
26. VIEIRA, J., and MESSING, J. (1982). Gene. 19, 259–268.

We claim:

1. A synthetic polypeptide which includes the conformational epitope recognized by monoclonal antibody MAb 17-82 and displays the antigenicity of the 41/37 Kd protein of IBDV serotype 1 such that said polypeptide is capable of eliciting IBDV neutralizing antibodies in an avian host.

2. A fused polypeptide comprising a synthetic polypeptide sequence which includes the conformational epitope recognized by monoclonal antibody MAb 17-82 and displays the antigenicity of the 41/37 Kd protein of IBDV serotype 1 as the C-terminal sequence, and an additional polypeptide coded for by the DNA of a recombinant DNA cloning vehicle or vector as the N-terrninal sequence fused thereto, such that the fused polypeptide is capable of eliciting IBDV neutralizing antibodies in an avian host.

3. A composition for stimulating an immune response against IBDV in an avian host, which comprises an immunogenic polypeptide together with a pharmaceutically acceptable carrier therefor, said immunogenic polypeptide being selected from the group consisting of:
1) a synthetic polypeptide which includes the conformational epitope recognized by monoconal antibody of MAb 17-82 and displays the antigenicity of the 41/37 Kd protein of IBDV serotype 1 such that said polypeptide is capable of eliciting IBDV neutralizing antibodies in said avian host; and
2) a fused polypeptide comprising a synthetic polypeptide sequence which includes the conformational epitope recognized by monoclonal antibody MAb 17-82 and displays the antigenicity of the 41/37 Kd protein of IBDV serotype 1 or of a fragment thereof as the C-terminal sequence and an additional polypeptide coded for by the DNA of a recombinant DNA cloning vehicle or vector as the N-terminal sequence fused thereto, such that the fused polypeptide is capable of eliciting IBDV neutralizing antibodies in said avian host.

4. A synthetic polypeptide which includes the conformationlal epitope recognized by monoclonal antibody MAb 17-82 and displays the antigenicity of the 41/37 Kd protein of IBDV serotype 1 such that said polypeptide is capable of eliciting IBDV neutralizing antibodies in an avian host; said synthetic polypeptide being substantially free of other IBDV proteins.

5. A fused polypeptide comprising a synthetic polypeptide sequence which includes the conformational epitope recognized by monoclonal antibody Mab 17-82 and displays the antigenicity of the 41/37 Kd protein of IBDV serotype 1 as the C-terminal sequence, and an additional polypeptide coded for by the DNA of a recombinant DNA cloning vehicle or vector as the N-terminal sequence fused thereto, such that the fused polypeptide is capable of eliciting IBDV neutralizing antibodies in an avian host; said fused polypeptide being substantially free of other IBDV proteins.

6. A composition for stimulating an immune response against IBDV in an avian host which comprises an immunogenic polypeptide in combination with a pharmaceutically acceptable carrier therefore; said immunogenic polypeptide being selected from the group consisting of:
1) a synthetic polypeptide which includes the conformational epitope recognized by monocioal antibody MAb 17-82 and displays the antigenicity of the 41/37 Kd protein of IBDV serotype 1 or such said polypeptide is capable of eliciting IBDV neutralizing antibodies in an avian host, said synthetic polypeptide being substantially free of other IBDV proteins; and
2) a fused polypeptide comprising a synthetic polypeptide sequence which includes the conformational epitope recognized by monoclonal antibody MAb 17-82 and displays the antigenicity of the 41/37 Kd protein of IBDV serotype 1 or as the C-terminal sequence, and an additional polypeptide coded for by the DNA of a recombinant DNA cloning vehicle or vector as the N-terminal sequence fused thereto, such that the fused polypeptide is capable of eliciting IBDV neutralizing antibodies in said avian host; said fused polypeptide being substantially free of other IBDV proteins.

7. A composition according to claim 6 which further comprises an adjuvant.

8. A composition according to claim 3 further comprising an adjuvant.

9. An isolated synthetic serotype 1 IBDV 41/37 kDa polypeptide which retains a conformational neutralizing epitope of the native, intact IBDV virus recognized by monoclonal antibody 17-82, absent from SDS detergent treated 41/37 kDa polypeptide, or a fragment of said polypeptide comprising a conformational neutralizing epitope absent from SDS detergent treated 41/37 kDa polypeptide.

10. The polypeptide of claim 9 which further comprises non-IBDV amino acid sequences encoded by a cloning vector.

11. A method of stimulating an immune response against IBDV in poultry, which comprises administering a composition according to claim 3 to said poultry.

12. A method for stimulating an immune response against IBDV in poultry which comprises administering a composition according to claim 6 to said poultry.

13. A method for stimulating an immune response against IBDV in poultry which comprises administering a composition according to claim 7 to said poultry.

14. A method for stimulating an immune response against IBDV in poultry which comprises administering a composition according to claim 8 to said poultry.

* * * * *